(12) United States Patent
Kitano et al.

(10) Patent No.: US 8,907,021 B2
(45) Date of Patent: *Dec. 9, 2014

(54) POLYACRYLIC ACID (SALT)-TYPE WATER ABSORBENT RESIN AND METHOD FOR PRODUCING OF SAME

(75) Inventors: Takahiro Kitano, Hyogo (JP); Kozo Nogi, Hyogo (JP); Kunihiko Ishizaki, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 99 days.

This patent is subject to a terminal disclaimer.

(21) Appl. No.: 13/392,639

(22) PCT Filed: Aug. 27, 2010

(86) PCT No.: PCT/JP2010/064646
§ 371 (c)(1),
(2), (4) Date: Feb. 27, 2012

(87) PCT Pub. No.: WO2011/024975
PCT Pub. Date: Mar. 3, 2011

(65) Prior Publication Data
US 2012/0157625 A1    Jun. 21, 2012

(30) Foreign Application Priority Data

| Aug. 27, 2009 | (JP) | 2009-196967 |
| Aug. 27, 2009 | (JP) | 2009-197022 |
| Aug. 27, 2009 | (JP) | 2009-197063 |
| Aug. 27, 2009 | (JP) | 2009-197091 |

(51) Int. Cl.
*C08F 2/01* (2006.01)

(52) U.S. Cl.
USPC .................................... 525/329.7; 525/23

(58) Field of Classification Search
USPC .................................................. 525/329.7
See application file for complete search history.

(56) References Cited

U.S. PATENT DOCUMENTS

| 4,734,478 A | 3/1988 | Tsubakimoto et al. |
| 4,755,562 A | 7/1988 | Alexander et al. |
| 4,783,510 A | 11/1988 | Saotome |
| 4,824,901 A | 4/1989 | Alexander et al. |
| 4,893,999 A | 1/1990 | Chmelir et al. |
| 5,124,416 A | 6/1992 | Haruna et al. |
| 5,140,076 A | 8/1992 | Hatsuda et al. |
| 5,206,205 A | 4/1993 | Tsai |
| 5,250,640 A | 10/1993 | Irie et al. |
| 5,409,771 A | 4/1995 | Dahmen et al. |
| 5,422,405 A | 6/1995 | Dairoku et al. |
| 5,610,208 A | 3/1997 | Dairoku et al. |
| 5,669,894 A | 9/1997 | Goldman et al. |
| 5,672,633 A | 9/1997 | Brehm et al. |
| 6,071,976 A | 6/2000 | Dairoku et al. |
| 6,228,930 B1 | 5/2001 | Dairoku et al. |
| 6,239,230 B1 | 5/2001 | Eckert et al. |
| 6,241,928 B1 | 6/2001 | Hatsuda et al. |
| 6,254,990 B1 | 7/2001 | Ishizaki et al. |
| 6,265,488 B1 | 7/2001 | Fujino et al. |
| 6,297,319 B1 | 10/2001 | Nagasuna et al. |
| 6,300,423 B1 | 10/2001 | Engelhardt et al. |
| 6,372,852 B2 | 4/2002 | Hitomi et al. |
| 6,472,478 B1 | 10/2002 | Funk et al. |
| 6,503,979 B1 | 1/2003 | Funk et al. |
| 6,514,615 B1 | 2/2003 | Sun et al. |
| 6,559,239 B1 | 5/2003 | Riegel et al. |
| 6,576,713 B2 | 6/2003 | Ishizaki et al. |
| 6,605,673 B1 | 8/2003 | Mertens et al. |
| 6,620,889 B1 | 9/2003 | Mertens et al. |
| 6,620,899 B1 | 9/2003 | Morken et al. |
| 6,657,015 B1 | 12/2003 | Riegel et al. |
| 6,710,141 B1 | 3/2004 | Heide et al. |
| 6,720,389 B2 | 4/2004 | Hatsuda et al. |

(Continued)

FOREIGN PATENT DOCUMENTS

| CN | 1530384 | 9/2004 |
| EP | 0349240 | 1/1990 |

(Continued)

OTHER PUBLICATIONS

International Search Report for PCT/JP2010/064646, dated Sep. 28, 2010.
Chinese Office Action, dated Jan. 15, 2013, in related CN Appln. No. 201080038386.5, and its English translation.
Chinese Office Action, dated Jan. 15, 2013, in related CN Appln. No. 201080038364.9, and its English translation.
Chinese Office Action, dated Sep. 17, 2013, in related CN Appln. No. 201080038364.9, and its English translation.

(Continued)

*Primary Examiner* — Doris Lee
(74) *Attorney, Agent, or Firm* — Roylance, Abrams, Berdo & Goodman, L.L.P.

(57) ABSTRACT

Disclosed is a method for producing a water absorbent resin, by which a surface-crosslinked water absorbent resin having excellent physical properties can be efficiently obtained at low cost, while assuring high productivity. When the production scale is increased to a continuous production at 1 t/hr or more, the physical properties are improved and stabilized (for example, standard deviation of the physical properties is reduced) by a surface-crosslinking treatment, and the absorption against pressure (AAP) and liquid permeability (SFC) are further improved. Specifically disclosed is a method for producing a water absorbent resin, which is characterized in that the stirring shaft of the continuous mixing apparatus for the surface-crosslinking agent is heated during the mixing step of the surface-crosslinking agent or that the continuous mixing apparatus for the surface-crosslinking agent is operated at a pressure that is reduced relative to the ambient pressure and a gas flow is passed through the mixing apparatus during the mixing of the surface-crosslinking agent so that the gas flow in the mixing apparatus is 40° C. or more (when defined with respect to the gas temperature at the exit).

14 Claims, 3 Drawing Sheets

(56) References Cited

U.S. PATENT DOCUMENTS

| | | |
|---|---|---|
| 6,809,158 B2 | 10/2004 | Ikeuchi et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,098,284 B2 | 8/2006 | Torii et al. |
| 7,157,141 B2 | 1/2007 | Inger et al. |
| 7,183,456 B2 | 2/2007 | Hatsuda et al. |
| 7,312,278 B2 | 12/2007 | Nakashima et al. |
| 7,378,453 B2 | 5/2008 | Nogi et al. |
| 7,473,739 B2 | 1/2009 | Dairoku et al. |
| 7,528,291 B2 | 5/2009 | Herfert et al. |
| 7,541,395 B2 | 6/2009 | Reimann et al. |
| 7,803,880 B2 | 9/2010 | Torii |
| 7,833,624 B2 | 11/2010 | Harren et al. |
| 7,851,550 B2 | 12/2010 | Kadonaga et al. |
| 7,893,134 B2 | 2/2011 | Reimann et al. |
| 7,910,675 B2 | 3/2011 | Funk et al. |
| 8,071,202 B2 | 12/2011 | Furno et al. |
| 2001/0025093 A1 | 9/2001 | Ishizaki et al. |
| 2004/0181031 A1 | 9/2004 | Nogi et al. |
| 2004/0240316 A1 | 12/2004 | Nogi et al. |
| 2005/0029352 A1 | 2/2005 | Spears |
| 2005/0048221 A1 | 3/2005 | Irie et al. |
| 2005/0051925 A1 | 3/2005 | Gartner et al. |
| 2005/0070671 A1 | 3/2005 | Torii et al. |
| 2005/0215734 A1 | 9/2005 | Dairoku et al. |
| 2005/0288182 A1 | 12/2005 | Torii et al. |
| 2006/0029782 A1 | 2/2006 | Harren et al. |
| 2006/0057389 A1 | 3/2006 | Reimann et al. |
| 2006/0073969 A1 | 4/2006 | Torii et al. |
| 2006/0252913 A1 | 11/2006 | Herfert et al. |
| 2006/0276598 A1 | 12/2006 | Wada et al. |
| 2007/0078231 A1 | 4/2007 | Shibata et al. |
| 2007/0106013 A1 | 5/2007 | Adachi et al. |
| 2007/0149760 A1* | 6/2007 | Kadonaga et al. ............ 528/480 |
| 2007/0161759 A1 | 7/2007 | Riegel et al. |
| 2007/0293632 A1 | 12/2007 | Riegel et al. |
| 2008/0221277 A1 | 9/2008 | Walden et al. |
| 2008/0227932 A1 | 9/2008 | Funk et al. |
| 2008/0280128 A1 | 11/2008 | Furno et al. |
| 2009/0105389 A1 | 4/2009 | Walden et al. |
| 2009/0202805 A1 | 8/2009 | Furno et al. |
| 2009/0209683 A1 | 8/2009 | Reimann et al. |
| 2009/0227741 A1 | 9/2009 | Walden et al. |
| 2009/0314258 A1 | 12/2009 | Azou |
| 2010/0072421 A1 | 3/2010 | Kitano et al. |
| 2010/0140546 A1 | 6/2010 | Barthel et al. |
| 2010/0249320 A1 | 9/2010 | Matsumoto et al. |
| 2011/0003926 A1 | 1/2011 | Nogi et al. |
| 2011/0006140 A1 | 1/2011 | Ishizaki et al. |
| 2011/0009590 A1 | 1/2011 | Matsumoto et al. |
| 2011/0011491 A1 | 1/2011 | Matsumoto et al. |
| 2011/0015351 A1 | 1/2011 | Nogi et al. |
| 2011/0028670 A1 | 2/2011 | Matsumoto et al. |
| 2011/0088806 A1 | 4/2011 | Nogi et al. |
| 2011/0110730 A1 | 5/2011 | Nogi et al. |
| 2011/0166300 A1 | 7/2011 | Dairoku et al. |

FOREIGN PATENT DOCUMENTS

| | | |
|---|---|---|
| EP | 0534228 | 3/1993 |
| EP | 0603292 | 6/1994 |
| EP | 1824910 | 8/2007 |
| JP | 54-010387 | 1/1979 |
| JP | 2-049002 | 2/1990 |
| JP | 3-168218 | 7/1991 |
| JP | 5-112654 | 5/1993 |
| JP | 5-202199 | 8/1993 |
| JP | 2000-143720 | 5/2000 |
| JP | 2002-121291 | 4/2002 |
| JP | 2004-300425 | 10/2004 |
| JP | 2004-345804 | 12/2004 |
| JP | 2004-352941 | 12/2004 |
| JP | 2004-359943 | 12/2004 |
| JP | 2006-503949 | 2/2006 |
| JP | 2006-522181 | 9/2006 |
| JP | 2006522181 | 9/2006 |
| JP | 2008-038128 | 2/2008 |
| JP | 2008-255366 | 10/2008 |
| JP | 2009-506151 | 2/2009 |
| JP | 2009-518484 | 5/2009 |
| WO | 2004/069915 | 4/2004 |
| WO | 2005/016393 | 2/2005 |
| WO | 2006/082188 | 8/2006 |
| WO | 2006/082189 | 8/2006 |
| WO | 2006/082197 | 8/2006 |
| WO | 2006/109842 | 10/2006 |
| WO | 2006/111402 | 10/2006 |
| WO | 2006/111403 | 10/2006 |
| WO | 2006/111404 | 10/2006 |
| WO | 2007/065840 | 6/2007 |
| WO | 2007/121037 | 10/2007 |
| WO | 2008/009842 | 1/2008 |
| WO | 2008/009843 | 1/2008 |
| WO | 2008/108277 | 9/2008 |
| WO | 2009/001954 | 12/2008 |
| WO | 2009/028568 | 3/2009 |
| WO | 2009/113672 | 9/2009 |
| WO | 2009/113673 | 9/2009 |
| WO | 2009/113679 | 9/2009 |

OTHER PUBLICATIONS

Chinese Office Action, dated Aug. 29, 2013, in related CN Appln. No. 201080038386.5, and its English translation.
Office Action dated Dec. 23, 2013 in U.S. Appl. No. 13/392,214.
Extended European Search Report dated Jan. 23, 2014 in EP 10812023.9.
Chinese Office Action dated Feb. 14, 2014 in CN 201080038386.5, and English translation thereof.
Office Action dated Jan. 7, 2014 in U.S. Appl. No. 13/392,240.
Japanese Notice of Reasons for Rejection dated Jun. 3, 2014 in JP 2011-528885, and English translation thereof.
English Machine Translation of JP 2008-038128 dated Feb. 21, 2008.
Office Action dated Jul. 22, 2014 in related U.S. Appl. No. 13/392,240.
Office Action dated Sep. 30, 2014 issued in U.S. Appl. No. 13/392,256.

* cited by examiner

POLYACRYLIC ACID (SALT)-TYPE WATER ABSORBENT RESIN AND METHOD FOR PRODUCING OF SAME

TECHNICAL FIELD

The present invention relates to a polyacrylic acid (salt)-type water absorbent resin and a method for producing the same. More particularly, the present invention relates to a polyacrylic acid (salt)-type water absorbent resin having high water absorption rate (CRC), high water absorption against pressure (AAP), and high liquid permeability (SFC) and containing little water extractables and a method for producing the same.

BACKGROUND ART

A water absorbent resin (Super Absorbent Polymer; abbreviated as SAP) has been used in a wide range of uses for sanitary materials such as paper diapers, sanitary napkins, incontinence products for adults, and the like, and uses for water retention agent for soil, owing to properties that the resin can absorb a large quantity of a water-based liquid several times to several hundred times as much as the mass of itself and has been manufactured and consumed in large quantities.

In general, a water absorbent resin is produced by polymerizing an aqueous solution containing a hydrophilic monomer and a crosslinking agent to obtain a hydrous gel-like polymer, drying the gel polymer, and surface-crosslinking the dried product. The physical properties such as water absorption against pressure (AAP) and liquid permeability (GBP, SFC) of the above-mentioned water absorbent resin are improved by surface-crosslinking step. The surface-crosslinking step is commonly a step of providing a highly crosslinked layer in the vicinity of the water absorbent resin surface by causing reaction of the water absorbent resin with a surface-crosslinking agent or a polymerizable monomer.

Various kinds of surface-crosslinking agents reactive on a functional group of a water absorbent resin (particularly, carboxyl group) are proposed as a surface-reforming method of such a water absorbent resin and examples known as the surface-crosslinking agents are oxazoline compounds (Patent Document 1), vinyl ether compounds (Patent Document 2), epoxy compounds (Patent Document 3), oxetane compounds (Patent Document 4), polyhydric alcohol compounds (Patent Document 5), polyamide polyamine-epihalo adducts (Patent Documents 6, 7), hydroxyacrylamide compounds (Patent Document 8), oxazolidinone compounds (Patent Documents 9, 10), bis- or poly-oxazoline compounds (Patent Document 11), 2-oxotetrahydro-1,3-oxazolidine compounds (Patent Document 12), alkylene carbonate compounds (Patent Document 13), and the like. A technique using a specified surface-crosslinking agent (Patent Document 14) is also known.

Techniques also known as the surface-reforming method other than the method carried out by a surface-crosslinking agent are a technique of surface-crosslinking by polymerizing a monomer in the vicinity of the water absorbent resin surface (Patent Document 15) and techniques of radical crosslinking with persulfuric acid salts etc. (Patent Documents 16, 17). Techniques of reforming water absorbent resins by heating without using a surface-crosslinking agent (Patent Documents 18, 19), which is different from common surface-crosslinking treatment, are also known.

A technique of using an additive in combination for mixing a surface-crosslinking agent is also proposed and examples known as the additive are water-soluble cations such as aluminum salts etc. (Patent Documents 20, 21), alkali (Patent Document 22), organic acids or inorganic acids (Patent Document 23), peroxides (Patent Document 24), and surfactants (Patent Document 25).

Not only the chemical methods but also many surface treatment methods using apparatuses and reaction conditions have been proposed. Examples known as a method using an apparatus are techniques using a specified mixing apparatus as a mixing apparatus for a surface-crosslinking agent (Patent Documents 26 to 29) and techniques using a heating apparatus for causing reaction of a water absorbent resin and a surface-crosslinking agent (Patent Documents 30, 31) and the like.

There is also a technique for controlling an increase in heating temperature for causing reaction of a water absorbent resin and a surface-crosslinking agent (Patent Document 32) in improvement of the reaction condition aspect. In a heating step, techniques known are a technique of carrying out surface-crosslinking twice (Patent Document 33), a technique of controlling particle size by drying a water absorbent resin, thereafter carrying out a second heat drying step, and further carrying out surface-crosslinking (Patent Document 34), a technique of defining oxygen partial pressure (Patent Document 35), techniques of defining the spraying conditions and dew points (Patent Documents 37, 38), techniques of defining the mixing conditions of treatment liquids (Patent Documents 39, 40), and a technique paying attention to a cooling step (Patent Document 41).

PRIOR ART DOCUMENTS

Patent Documents

Patent Document 1: U.S. Pat. No. 6,297,319
Patent Document 2: U.S. Pat. No. 6,372,852
Patent Document 3: U.S. Pat. No. 6,265,488
Patent Document 4: U.S. Pat. No. 6,809,158
Patent Document 5: U.S. Pat. No. 4,734,478
Patent Document 6: U.S. Pat. No. 4,755,562
Patent Document 7: U.S. Pat. No. 4,824,901
Patent Document 8: U.S. Pat. No. 6,239,230
Patent Document 9: U.S. Pat. No. 6,559,239
Patent Document 10: U.S. Pat. No. 6,503,979
Patent Document 11: U.S. Pat. No. 6,472,478
Patent Document 12: U.S. Pat. No. 6,657,015
Patent Document 13: U.S. Pat. No. 5,409,771
Patent Document 14: U.S. Pat. No. 5,422,405
Patent Document 15: US Patent Application Publication No. 2005/048221
Patent Document 16: U.S. Pat. No. 4,783,510
Patent Document 17: EP Patent No. 1824910
Patent Document 18: U.S. Pat. No. 5,206,205
Patent Document 19: EP Patent No. 0603292
Patent Document 20: U.S. Pat. No. 6,605,673
Patent Document 21: U.S. Pat. No. 6,620,899
Patent Document 22: U.S. Pat. No. 7,312,278
Patent Document 23: U.S. Pat. No. 5,610,208
Patent Document 24: US Patent Application Publication No. 2007/078231
Patent Document 25: US Patent Application Publication No. 2005/029352
Patent Document 26: U.S. Pat. No. 5,140,076
Patent Document 27: U.S. Pat. No. 6,071,976
Patent Document 28: US Patent Application Publication No. 2004/240316
Patent Document 29: WO No. 2007/065840 pamphlet Patent Document 30: US Patent Application Publication No. 2007/149760
Patent Document 31: Japan Patent Application Publication No. 2004-352941
Patent Document 32: U.S. Pat. No. 6,514,615
Patent Document 33: U.S. Pat. No. 5,672,633
Patent Document 34: WO No. 2009/028568 pamphlet
Patent Document 35: US Patent Application Publication No. 2007/0293632
Patent Document 36: U.S. Pat. No. 6,720,389
Patent Document 37: U.S. Pat. No. 7,183,456
Patent Document 38: US Patent Application Publication No. 2007/161759
Patent Document 39: US Patent Application Publication No. 2006/057389
Patent Document 40: EP Patent No. 0534228
Patent Document 41: U.S. Pat. No. 7,378,453

DISCLOSURE OF THE INVENTION

Problems to be Solved by the Invention

It is difficult to satisfy demands from users for physical properties such as water absorption against pressure and liquid permeability of a water absorbent resin only by a surface-crosslinking technique, although there have been proposed many of surface-crosslinking agents (see Patent Documents 1 to 13) and their combination use (see Patent Document 14), auxiliary agents for surface-crosslinking (see Patent Documents 20 to 25), their mixing apparatuses (see Patent Documents 26 to 29) and heating apparatuses (Patent Documents 30, 31), and also various kinds of conditions (see Patent Documents 32 to 41). Along with change of a surface-crosslinking agent and use of a new auxiliary agent, it may be sometimes accompanied with an increase in cost, a decrease in safety, deterioration of other physical properties (e.g., coloration), and the like in some cases. Although causing an effect to a certain extent in a small scale or batch type production in an experimental laboratory level, the above-mentioned means may not sometimes show so much effective in an industrial scale (e.g., 1 t or more per unit hour) such as large scale continuous production as compared with that in a small scale.

The present invention has been completed in terms of the problems, and an object of the present invention is to provide a method for producing a water absorbent resin which is excellent in physical properties and surface-crosslinked efficiently at a low cost while assuring high productivity.

Solutions to the Problems

The inventors of the present invention have made investigations on a surface-crosslinking step for solving the above-mentioned problems and consequently have solved the problems by carrying out mixing in a specified condition in a wetting and mixing step for adding a surface-crosslinking agent.

That is, the present invention provides a method (first method) for producing a polyacrylic acid (salt)-type water absorbent resin comprising steps of:
preparing an aqueous monomer solution of an acrylic acid (salt),
continuously polymerizing the aqueous monomer solution,
finely shredding a hydrous gel-like crosslinked polymer during or after polymerization,
drying the obtained particulate hydrous gel-like crosslinked polymer,
adding a surface-crosslinking agent to the dried water absorbent resin powder with a continuous mixing apparatus, and
carrying out reaction of the mixture, wherein
a stirring shaft of the continuous mixing apparatus for the surface-crosslinking agent is heated in the step of mixing the surface-crosslinking agent.

Also the present invention provides a method (second method) for producing a polyacrylic acid (salt)-type water absorbent resin comprising steps of:
preparing an aqueous monomer solution of an acrylic acid (salt),
continuously polymerizing the aqueous monomer solution,
finely shredding a hydrous gel-like crosslinked polymer during or after polymerization,
drying the obtained particulate hydrous gel-like crosslinked polymer,
adding a surface-crosslinking agent to the dried water absorbent resin powder with a continuous mixing apparatus, and
carrying out reaction of the mixture, wherein
the continuous mixing apparatus for the surface-crosslinking agent is operated in pressure decreased from the ambient pressure and gas current to adjust the outlet gas temperature of the gas current in the mixing apparatus to be at lowest 40° C. is led to the mixing apparatus during mixing the surface-crosslinking agent.

In addition, the first method and the second method are preferably employed in combination.

Effects of the Invention

According to the present invention, in continuous production in a large industrial scale (particularly, treatment amount of 1 t/hr or more), the physical properties (e.g., water absorption against pressure and liquid permeability) can be improved after surface-crosslinking and the fluctuation of physical property (standard deviation) can be narrowed.

MODE FOR CARRYING OUT THE INVENTION

Figure 1:
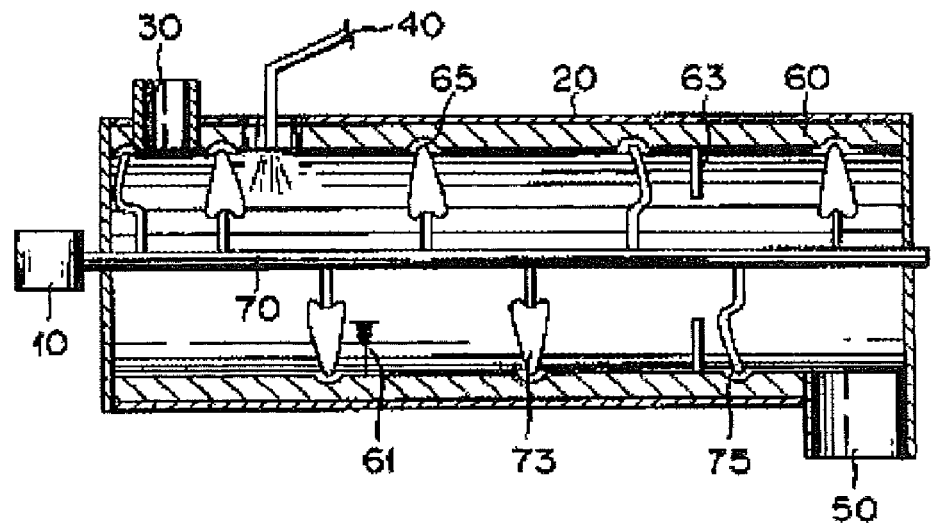
FIG. 1 is a schematic view showing in one example of a hoe-type continuous mixing apparatus preferably usable in a surface-crosslinking method of the present invention.

Hereinafter, the polyacrylic acid (salt)-type water absorbent resin of the present invention and a method for producing the same will be described in detail; however, the scope of the present invention is not restricted to the following description, and those other than the following examples can be properly modified and carried out in a range where the gist of the present invention is not impaired. Specifically, the present invention is not limited to each of the following embodiments, and various modifications can be made within a range shown by the claims and embodiments carried out by properly combining each technical means disclosed with different embodiments are also included within the technical scope of the present invention.

[1] Definition of Terms (a) "Water Absorbent Resin"

The "water absorbent resin" means water-swelling and water-insoluble "polymer gelling agent" and includes those having the following physical properties. That is, those having, as the water-swelling property, a water absorption rate under no pressure (CRC) of 5 g/g or more. CRC is preferably 10 to 100 g/g and more preferably 20 to 80 g/g. Because of water-insolubility, it is required that water extractables are in amount of 0 to 50 mass %. The water extractables are preferably in amount of 0 to 30 mass %, more preferably in amount of 0 to 20 mass %, and even preferably in amount of 0 to 10 mass %.

The water absorbent resin is not limited to be embodiments of 100 mass % of a polymer and may contain other additives (described below) to the extent of retaining the above-mentioned characteristics. That is, even a water absorbent resin composition having the water absorbent resin and additives is generally named as a water absorbent resin in the present invention. The content of the polyacrylic acid (salt)-type water absorbent resin is preferably 70 to 99.9 mass % relative to the entire water absorbent resin, more preferably 80 to 99.7 mass %, and still more preferably 90 to 99.5 mass %. The components other than the water absorbent resin are preferably water in terms of the water absorption speed and impact resistance of powder (particles) and may include, if necessary, additives described below.

(b) "Polyacrylic Acid (Salt)"

The "polyacrylic acid (salt)" means a polymer containing arbitrarily a graft component and, as a repeating unit, an acrylic acid (salt) as a main component. The acrylic acid (salt) as a monomer excluding a crosslinking agent is in an amount of essentially 50 to 100% by mole, preferably 70 to 100% by mole, more preferably 90 to 100% by mole, and still more preferably substantially 100% by mole. The acrylic acid salt as the polymer essentially contains a polyacrylic acid salt and preferably contains a monovalent salt, more preferably an alkali metal salt or ammonium salt, still more preferably an alkali metal salt, and particularly preferably sodium salt. The shape is not particularly limited; however, the polyacrylic acid (salt) is preferably particles or a powder.

(c) "EDANA" and "ERT"

"EDANA" is an abbreviation of European Disposables and Nonwovens Associations. "ERT" is an abbreviation of measurement method (ERT/EDANA Recommended Test Method) of a water absorbent resin on the basis of European Standards (almost Global Standards) as defined below. In this specification, unless otherwise specified, the physical properties of a water absorbent resin are measured based on ERT original text (Known Document: revised in 2002).

(c-1) CRC (ERT441.2-02)

The "CRC" is an abbreviation for Centrifuge Retention Capacity and means water absorption rate under no pressure (simply sometimes referred to as "water absorption rate").

Specifically, the CRC is the water absorption rate (unit; g/g) after 0.200 g of a water absorbent resin in a nonwoven fabric bag is freely swollen in 0.9 mass % saline solution for 30 minutes and dewatered by a centrifuge at 250 G.

(c-2) AAP (ERT442.2-02)

The "AAP" is an abbreviation for Absorption Against Pressure and means water absorption against pressure. Specifically, the APP is the water absorption rate (unit; g/g) after 0.900 g of a water absorbent resin is swollen in 0.9 mass % saline solution for 1 hour under 1.9 kPa load. In the present invention and examples, the measurement is carried out at 4.8 kPa.

(c-3) "Extractables" (ERT 470.2-02)

"Extractables" means the amount of water soluble components (dissolve amount). Specifically, measurement is carried out by adding 1.000 g of the water absorbent resin to 200 ml of an 0.9 mass % aqueous saline solution, stirring the solution for 16 hours, and measuring the amount of a dissolved polymer by pH titration (unit: mass %).

(c-4) Residual monomers (ERT410.2-02)

The "residual monomers" means the amount of monomers remaining in a water absorbent resin. Specifically, the amount of monomers is a value (unit; ppm by mass) obtained by measuring, after 1.000 g of a water absorbent resin is charged to 200 $cm^3$ of 0.9 mass % saline solution and the resultant is stirred for 2 hours, the amount of monomers eluted in the aqueous solution by using high-pressure liquid chromatography.

(c-5) PSD (ERT420.2-02)

The "PSD" is an abbreviation for Particle Size Distribution and means the particle size distribution measured by sieving classification. The mass average particle diameter and the particle diameter distribution width can be measured by the same method as in "(1) Average Particle Diameter and Distribution of Particle Diameter" described in European Patent No. 0349240, p. 7, lines 25-43 and WO 2004/069915.

(c-6) Others "pH" (ERT400.2-02): The "pH" means pH of a water absorbent resin.

"Moisture Content" (ERT 430.2-02): The moisture content means the water content of a water absorbent resin.

"Flow Rate" (ERT 450.2-02): The flow rate means the flow down speed of a water absorbent resin powder.

"Density" (ERT 460.2-02): The density means the bulk specific density of a water absorbent resin.

(d) "Liquid Permeability"

The "liquid permeability" means the flow of a liquid flowing among particles of swollen gel under a load or no load. The "liquid permeability" can be measured by SFC (Saline Flow Conductivity) or GBP (Gel Bed Permeability) as a representative measurement method.

The "SFC" is liquid permeability of 0.69 mass % physiological saline solution in a water absorbent resin at a load of 0.3 psi. It is measured according to an SFC testing method described in U.S. Pat. No. 5,669,894.

The "GBP" is liquid permeability of 0.69 mass % physiological saline solution in a water absorbent resin under a load or free expansion. It is measured according to a GBP testing method described in WO 2005/016393 pamphlet.

(e) "Standard Deviation"

The "standard deviation" is a numeral value showing the degree of dispersion of data and means a positive square root of the value calculated by totalizing the square value of the difference of the value of n samples and their arithmetic average, that is, the deviation, and dividing the total by n−1. It is used for understanding the degree of fluctuation for the phenomenon with considerable fluctuation. In this specification, the standard deviation is employed for digitalization of the fluctuation (deflection) for a desired physical value of interest.

$$\text{Data of } n \text{ samples } x1, x2, \ldots xn \quad \text{[Numeral 1]}$$

$$\text{Arithmetic average } X = \frac{1}{N}\sum_{i=1}^{n} Xi$$

$$\text{Standard deviation} = \sqrt{\frac{1}{n-1}\sum_{i=1}^{n}(Xi-X)^2}$$

(f) Others

In this specification, "X to Y" showing a range means "X or more and Y or lower". Additionally, the unit of mass "t (ton)" means "Metric ton". Further, the measurement of physical properties of a water absorbent resin is carried out under the conditions of a temperature of 20 to 25° C. (sometimes simply referred to as "room temperature" or "normal temperature") and a relative humidity of 40 to 50%, unless otherwise stated.

[2] a Method for Producing Polyacrylic Acid (Salt)-Type Water Absorbent Resin (1) Polymerization Step (a) Monomer (Excluding a Crosslinking Agent)

A monomer of the present invention contains the above-mentioned acrylic acid or its salt as a main component and in terms of water absorption characteristics and decrease of the residual monomers, the acid groups of a polymer are preferable to be neutralized and the neutralization ratio is 10 to 100% by mole preferable, more preferably 30 to 95% by mole, still more preferably 50 to 90% by mole, and particularly preferably 60 to 80% by mole. The neutralization may be carried out for the polymer (hydrous gel) after polymerization or for the monomer; however, in terms of productivity and improvement of AAP, neutralization of the monomer is preferable. Consequently, the monomer in the present invention includes a partially neutralized salt of the acrylic acid.

Further, in the present invention, a hydrophilic or hydrophobic unsaturated monomer may be used besides an acrylic acid (salt). Monomers usable may include methacrylic acid, maleic acid, maleic anhydride, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol(meth)acrylate, polyethylene glycol(meth)acrylate, stearyl acrylate, and their salts.

(b) Crosslinking Agent (Inner Crosslinking Agent)

In the present invention, in terms of the water absorbent properties, use of a crosslinking agent (i.e.; inner crosslinking agent) is preferable. The crosslinking agent is used in an amount of preferably 0.001 to 5% by mole, more preferably 0.005 to 2% by mole, still more preferably 0.01 to 1% by mole, and particularly preferably 0.03 to 0.5% by mole to the monomer excluding the crosslinking agent, in terms of physical aspect.

Examples usable as the crosslinking agent are one or more of polymerizable crosslinking agents (with polymerizable double bond of the acrylic acid), reactive crosslinking agents (with a carboxyl group of the monomer), and crosslinking agents having both of these properties. Concrete examples are, as a polymerizable crosslinking agent, compounds having at least two polymerizable double bonds in a molecule such as N,N'-methylenebisacrylamide, (poly)ethylene glycol di(meth)acrylate, (polyoxyethylene)trimethylolpropane tri(meth)acrylate, poly(meth)allyloxyalkanes, etc. Further, examples of the reactive crosslinking agent are covalent-binding crosslinking agents such as polyglycidyl ether (ethylene glycol diglycidyl ether or the like), poly alcohols (propanediol, glycerin, sorbitol, etc.), and ion-binding crosslinking agents such as polyvalent metal compounds of aluminum or the like. Among these crosslinking agents, in terms of water absorbent properties, polymerizable crosslinking agents (with the acrylic acid), particularly, acrylate type, allyl type, and acrylamide type polymerizable crosslinking agents are preferably used.

(c) Neutralizing Salt

Preferable examples as a basic substance to be used for neutralization of the acrylic acid may include monovalent bases such as alkali metal hydroxides such as sodium hydroxide, potassium hydroxide, and lithium hydroxide etc., and alkali metal (hydrogen) carbonates such as sodium (hydrogen) carbonate, potassium (hydrogen) carbonate, etc. Particularly, in terms of decrease of the residual monomers, neutralization into an alkali metal acrylate especially with sodium hydroxide is preferable. The preferable conditions or the like in these neutralization treatments are exemplified in JP 2006/522181 and the disclosed conditions are applicable for the present invention. The neutralization temperature is preferably in a range of 10 to 100° C., more preferably in a range of 30 to 90° C.

The neutralization temperature is properly determined in this range, and a neutralization method described below is preferable to decrease the residual monomers.

(d) Concentration of Monomer

Monomers may be polymerized generally in an aqueous solution. The solid content is generally 10 to 90 mass %, preferably 20 to 80 mass %, more preferably 30 to 70 mass %, and particularly preferably 35 to 60 mass %. The polymerization may be carried out in the form of a slurry (water dispersion liquid) exceeding the saturated concentration; however, in terms of physical properties, it is carried out in an aqueous solution with the saturated concentration or lower.

(e) Other Monomer Components

The aqueous unsaturated monomer solution may contain a water-soluble resin or a water absorbent resin such as starch, polyacrylic acid (salt), or polyethylene imine, in combination with a monomer, in an amount of, for example, 0 to 50 mass %, preferably 0 to 20 mass %, particularly preferably 0 to 10 mass %, and most preferably 0 to 3 mass %. The solution may further contain a various kinds of foaming agents (carbonates, azo compounds, air bubbles, etc.), surfactants, or additives described below, in an amount of, for example, 0 to 5 mass % and preferably 0 to 1 mass % to improve the various physical properties of a water absorbent resin or particulate water absorbent agent to be obtained. A graft polymer obtained by using other components (e.g., starch-acrylic acid graft polymer) or a water absorbent resin composition is also generically referred to as a polyacrylic acid (salt)-type water absorbent resin in the present invention.

As the additive, a chelating agent, hydroxycarboxylic acid, or a reducing inorganic salt may be added, and it may be added to the water absorbent resin in such a manner that the amount thereof is preferably 10 to 5000 ppm by mass, more preferably 10 to 1000 ppm by mass, still more preferably 50 to 1000 ppm by mass, and particularly preferably 100 to 1000 ppm by mass. A chelating agent is preferable to be used.

The monomer is also preferable to contain a polymerization inhibitor. Examples of the polymerization inhibitor include methoxyphenol etc. and the content thereof is preferably 200 ppm or lower, more preferably 10 to 160 ppm, and still more preferably 20 to 100 ppm (relative to monomer).

(f) Polymerization Step (Crosslinking Polymerization Step)

Owing to the performance and the easiness of polymerization control, the polymerization method may be carried out by spray polymerization or droplet polymerization, but preferably, in general, it is carried out by aqueous solution polymerization or reverse phase suspension polymerization. The aqueous solution polymerization is preferably which are conventionally difficult to control polymerization or improve the coloring, and further preferably continuous aqueous solution polymerization. An especially preferable controlling method is a continuous polymerization method for producing the water absorbent resin in a huge scale of 0.5 t/h or higher, further 1 t/h or higher, still more 5 t/hr or higher, and still further 10 t/hr or higher by polymerization of an aqueous unsaturated monomer solution in one line. Consequently, the preferable continuous polymerization may include methods described as continuous kneader polymerization (e.g. U.S. Pat. Nos. 6,987,151 and 6,710,141), continuous belt polymerization (e.g. U.S. Pat. Nos. 4,893,999 and 6,241,928, and US Patent Application Publication No. 2005/215734).

In addition, in the continuous polymerization, polymerization at a high temperature starting (monomer at 30° C. or higher, 35° C. or higher, further 40° C. or higher, and particularly 50° C. or higher: the upper limit is the boiling point) or a high monomer concentration (30 mass % or higher, 35 mass % or higher, further 40 mass % or higher, and particularly 45 mass % or higher: the upper limit is the saturated concentration) can be exemplified as one preferable example.

The monomer stability is excellent in the present invention and the water absorbent resin with white color can be obtained even by the polymerization in such a high concentration and at such a high temperature, and thus the effect is significantly exhibited in such conditions. Preferable examples of high temperature initiating polymerization are described in U.S. Pat. Nos. 6,906,159 and 7,091,253 etc. In the present invention, the monomer stability before polymerization is excellent and therefore, production in an industrial scale is made easy.

The polymerization can be carried out in atmospheric air; however, it is preferable for coloring improvement to carry out the polymerization in an inert gas atmosphere of nitrogen or argon (e.g., oxygen concentration of 1% by volume or lower) and also, the monomer is preferable to be used for polymerization after the dissolved oxygen in the monomer or the solution containing the monomer is sufficiently replaced with an inert gas (e.g., less than 1 mg/L of dissolved oxygen). Even if such degassing is carried out, the monomer is excellent in the stability and therefore gelatinization before the polymerization does not occur and the water absorbent resin with higher physical properties and high whiteness can be obtained.

(g) Polymerization Initiator

A polymerization initiator to be used for the present invention can be selected properly in accordance with the polymerization mode. Examples of the polymerization initiator may include radical polymerization initiator such as a photodecomposition type polymerization initiator, a heat decomposition type polymerization initiator, and a redox type polymerization initiator. The amount of the polymerization initiator may be 0.0001 to 1% by mole preferably and more preferably 0.001 to 0.5% by mole to the monomer.

In the case of the amount of the polymerization initiator is large, coloring may possibly generate and in the case of the amount is low, it results in increase of the residual monomer. Further, in the case of a conventional coloring-improve agent, it sometimes causes a negative effect on the polymerization; however, in the polymerization by the method of the invention, the coloring can be improved without causing any negative effect on the polymerization (such as previous time and the various physical properties) and therefore, it is preferable.

Examples of the photodecomposition type polymerization initiator may include benzoin derivatives, benzyl derivatives, acetophenone derivatives, benzophenone derivatives, and azo compounds. Examples of the heat decomposition type polymerization initiator may include persulfuric acid salts (sodium persulfate, potassium persulfate, and ammonium persulfate), peroxides (hydrogen peroxide, tert-butyl peroxide, methyl ethyl ketone peroxide), azo compounds (2,2'-azobis (2-amindinopropane)dihydrochloride, 2,2'-azobis[2-(2-imidazolin-2-yl)propane]dihydrochloride, etc.). Among these radical polymerization initiators, persulfuric acid salts, peroxides, and azo compounds can be used as a photopolymerization initiator.

Examples of the redox type polymerization initiator may include the above-mentioned persulfuric acid salts or peroxides in combination with reducing compounds such as L-ascorbic acid and sodium hydrogen sulfite. Further, combination use of a photodecomposition type initiator and a heat decomposition type polymerization initiator can also be exemplified as a preferable embodiment.

(2) Gel Shredding Step (Pulverization Step)

A hydrous gel-like crosslinked polymer obtained by polymerization (hereinafter, sometimes referred to as "hydrous gel") may be dried as it is; however, it may be pulverized to be particulate (e.g., with a mass average particle diameter of 0.1 to 5 mm, preferably 0.5 to 3 mm) during polymerization or after polymerization with a pulverizer (kneader, meat chopper, or the like) if necessary.

From the physical property aspect, regarding the temperature of the hydrous gel at the time of gel pulverizing, the hydrous gel is kept or heated preferably at 40 to 95° C. and more preferably 50 to 80° C. The resin solid content of the hydrous gel is not particularly limited; however, from the physical property aspect, it is preferably 10 to 70 mass %, more preferably 15 to 65 mass %, and still more preferably 30 to 55 mass %. It is optional to add water, a polyhydric alcohol, a mixed liquid of water and a polyhydric alcohol, a solution obtained by dissolving a polyvalent metal in water, or their vapor, or the like. In the gel shredding step, a water absorbent resin fine powder or various kinds of other additives may be kneaded.

(3) Drying Step

In order to accomplish a decrease in residual monomers, prevention of gel deterioration (urea resistance), and prevention of yellowing in the present invention, the drying step is carried out via the gel shredding step after completion of the polymerization. The time until the start of drying via the gel shredding step is more preferable as it is shorter. That is, after being discharged out of the polymerization apparatus, a hydrous gel-like crosslinked polymer after polymerization starts to be dried preferably within 1 hour, more preferably within 0.5 hours, and still more preferably within 0.1 hours (charged to a drier). In order to set the time within the range, shredding or drying is preferably carried out directly without carrying out a storage step for the gel after polymerization. Further, to decrease the residual monomer and accomplish low coloring, the temperature of the a hydrous gel-like crosslinked polymer from completion of the polymerization to starting of the drying is controlled preferably at 50 to 80° C. and more preferably at 60 to 70° C.

The drying step provides a dried product having a resin solid content, which is calculated from a drying loss of the polymer (drying of 1 g powder or particles at 180° C. for 3 hours) in an amount controlled to be preferably 80 mass % or higher, more preferably 85 to 99 mass %, still more preferably 90 to 98 mass %, and particularly preferably 92 to 97 mass %. The drying temperature is not particularly limited; however, it is preferably in a range of 100 to 300° C. and more preferably in a range of 150 to 250° C. To satisfy both of the high physical properties and whiteness, it is preferably that the drying temperature is 160 to 235° C., more preferably 165 to 230° C. Further the drying time is preferably within 50 minutes. If the temperature or the time is out of the above-mentioned range, it may possibly result in decrease of the water absorption rate (CRC), increase of soluble matters (extractables), and deterioration of whiteness index.

A various drying methods such as heat drying, hot-air drying, vacuum drying, infrared drying, microwave drying, drying by a drum drier, azeotropic dehydration with a hydrophobic organic solvent, high humidity drying using high temperature steam can be employed. It is preferably hot-air drying with a gas with a dew point of preferably 40 to 100° C. and more preferably 50 to 90° C.

(4) Crushing and/or Classifying Step (Particle Size Adjustment after Drying)

After the drying step, the above-mentioned hydrous gel-like crosslinked polymer, the particle size may be adjusted after the drying if necessary. The polymer is preferably made to have a specified particle size to improve the physical properties by surface crosslinking described below. The particle size can be adjusted properly by polymerization (particularly reversed phase suspension polymerization), crushing, classification, granulation, and fine powder recovery. Hereinafter, the particle size is defined by a standard sieve (JIS Z8801-1 (2000)).

The mass average particle diameter (D50) of the obtained water absorbent resin particles in the dried step before surface crosslinking is adjusted to be 200 to 600 μm, preferably 200 to 550 μm, more preferably 250 to 500 and particularly preferably 350 to 450 μm. It is more preferable as the particles smaller than 150 μm are less, and the particles are adjusted in a range of generally 0 to 5 mass %, preferably 0 to 3 mass %, and more preferably 0 to 1 mass %. Further, it is more preferable as the particles bigger than 850 μm are less, and the particles are adjusted in a range of generally 0 to 5 mass %, preferably 0 to 3 mass %, and more preferably 0 to 1 mass %. The logarithmic standard deviation (σζ) of the particle size distribution is preferably 0.20 to 0.40, more preferably 0.25 to 0.37, and particularly preferably 0.27 to 0.35. Its measurement method may be a method described in, for example, International Publication No. 2004/69915 and a method described in EDANA-ERT 420.2-02 by using a standard sieve. The particle diameter is preferably applied also to the finally obtained water absorbent resin after surface crosslinking.

In general if the particle size distribution is narrowed, that is, the upper and lower limits of the particle size are controlled to be narrow, the color becomes noticeable; however, the present invention is free from such color issue and is preferable. Accordingly, in the present invention, it is preferable to carry out a classification step to give the ratio of particles with 150 to 850 μm of 90 mass % or more, more preferably 95 mass % or more, particularly preferably 98 mass % (The upper limit is 100 mass %) or more, after drying.

The bulk specific gravity of the water absorbent resin particles is preferably 0.5 to 0.75 (g/cm$^3$) and more preferably 0.6 to 0.7 (g/cm$^3$). A measurement method thereof is described in detail in, for example, EDANA ERT 460.2-02. In the case where the bulk specific gravity is not satisfied, the stirring power index becomes difficult to be controlled or the physical properties may be lowered or powdering may be caused in some cases.

(5) Surface Treatment Step

The feature of the present invention is in a method for producing a polyacrylic acid (salt)-type water absorbent resin comprising steps of:

preparing an aqueous monomer solution of an acrylic acid (salt), continuously polymerizing the aqueous monomer solution, finely shredding a hydrous gel-like crosslinked polymer during or after polymerization, drying the obtained particulate hydrous gel-like crosslinked polymer, adding and mixing a surface-crosslinking agent to the dried water absorbent resin powder with a continuous mixing apparatus, and carrying out reaction of the mixture, wherein a stirring shaft of the continuous mixing apparatus for the surface-crosslinking agent is heated in the surface-crosslinking agent mixing step.

or the continuous mixing apparatus for the surface-crosslinking agent is operated in pressure decreased from the ambient pressure and gas current to adjust the outlet gas temperature of the gas current in the mixing apparatus to be at lowest 40° C. is led to the mixing apparatus during mixing the surface-crosslinking agent.

(5-1) Humidifying and Mixing Step

This humidifying and mixing step is a step of adding and mixing a surface-crosslinking agent to and with the water absorbent resin powder obtained through the polymerization step to the finely shredding a hydrous gel-like crosslinked polymer step, the drying step and the classification step if applicable.

(a) Temperature of Stirring Shaft of Continuous Mixing Apparatus

Figure 3:
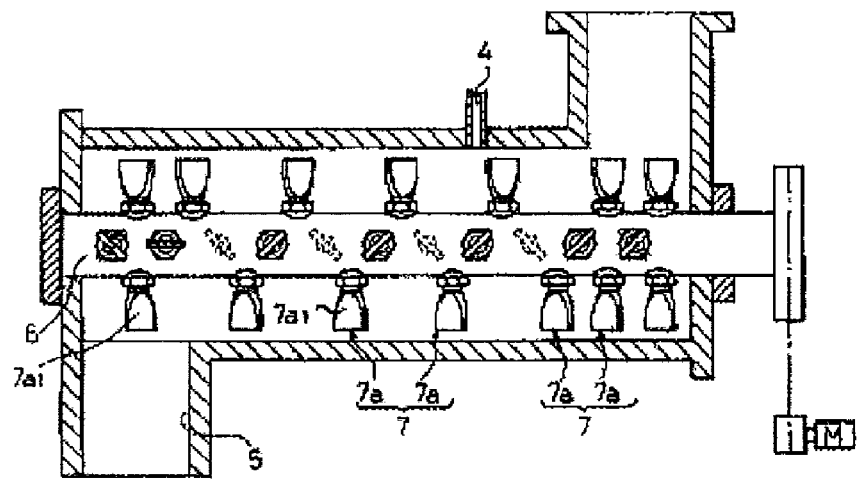
FIG. 3 is a schematic view showing one example of a continuous mixing apparatus other than a hoe-type one. Reference numeral 2 represents an inner wall, 6 represents a stirring shaft, and 7 (7a, 7b) represents a stirring blade in FIG. 3.
Figure 4:
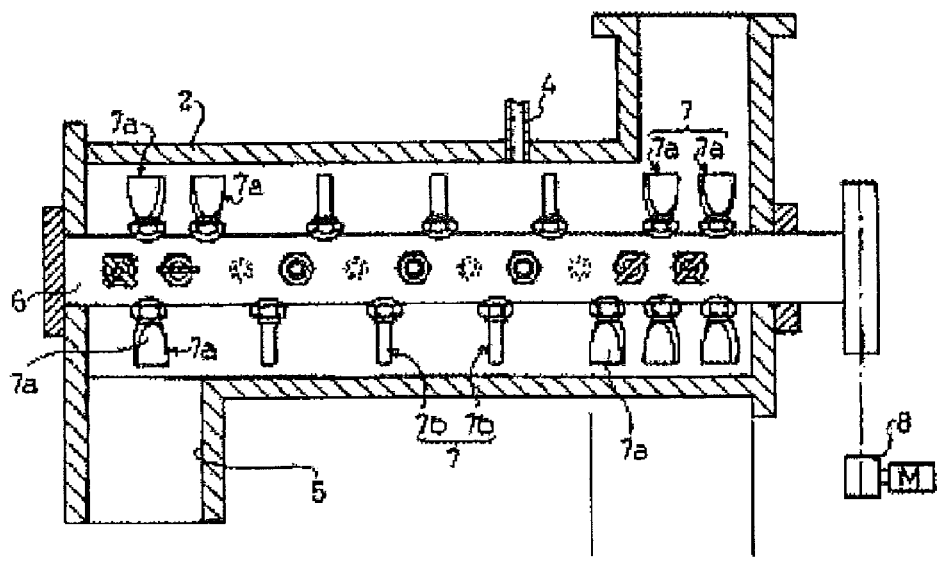
FIG. 4 is a schematic view showing one example of a continuous mixing apparatus other than a hoe-type one. Reference numeral 2 represents an inner wall, 6 represents a stirring shaft, and 7 (7a, 7b) represents a stirring blade in FIG. 4.

To solve the problems, in the present invention, a stirring shaft of a mixing apparatus is heated to room temperature or higher. A stirring shaft is shown, for example, with the reference numeral 70 in FIG. 1 and the reference numeral 6 in FIGS. 3 and 4, but not limited to these. Herein, the heating of the stirring shaft is generally 50° C. or higher and the upper limit is about 250° C. The temperature of the stirring shaft is preferably 90 to 170° C. and more preferably 100 to 150° C. Herein, the heating is indispensably carried out for the stirring shaft and preferably, stirring blades or stirring discs (e.g., shown by the reference numeral 73 in FIG. 1 and the reference numeral 7 (7a, 7b) in FIGS. 2, 3 and 4) are also heated. It is also preferable that the stirring shaft of the mixing apparatus is heated to a higher temperature than that of the inner wall (e.g., shown by the reference numeral 60 of FIG. 1 and the reference numeral 2 of FIG. 4). The temperature difference between the stirring shaft and the inner wall is more preferably exceeding 0° C. and not higher than 200° C., still more preferably 5 to 100° C., particularly preferably 10 to 90° C., and most preferably 15 to 80° C. It is found that in the case where no heating is carried out for the stirring shaft, the physical properties are deteriorated and become unstable by the surface-crosslinking (deterioration and fluctuation with the lapse of time and increase of standard deviation). It is also found that in the case where no heating is carried out for the shaft, a water absorbent resin containing a surface-crosslinking agent are gradually stuck to the shaft and rotating blades and further grown during long time operation and therefore, the mixing property of the surface-crosslinking agent is deteriorated and the physical properties (particularly, AAP/SFC) are gradually deteriorated. In the worst case, the mixing apparatus may possibly be stopped because of the excess load due to the adhesion. Since such a phenomenon depending on the execution of heating of the shaft is particularly significant in a hoe type mixing apparatus (e.g., shown in FIGS. 1 and 2), a hoe type mixing apparatus having a hoe type stirring blade (e.g., shown in FIG. 2) is suitably employed in the present invention.

The heating may be carried out partially or entirely for the stirring shaft; however, it is preferably for 50 to 100%, more preferably for 70 to 100%, still more preferably for 90 to 100%, and particularly preferably substantially 100% of the surface area of the stirring shaft. In the case where no heating is carried out for the shaft, the physical properties (e.g., the water absorption against pressure represented by AAP, and liquid permeability represented by SFC and GBP) may possibly be deteriorated and become instable (e.g., increase of standard deviation) after the surface-crosslinking and therefore, no effect of the present invention is exerted. On the other hand, if the shaft is heated to an excess extent, it is not only disadvantageous in terms of the installation cost but also it results in promotion of the reaction of a surface-crosslinking agent in the mixing apparatus, particularly to an excess extent before flowing in a heating device in the downstream stage and therefore the physical properties of the water absorbent resin may possibly be deteriorated in some cases.

In addition, in the present invention, a surface-crosslinking agent is reacted in a heating device, but it does not mean exclusion of the reaction in a mixing apparatus. The reaction of a surface-crosslinking agent can be confirmed in accordance with the physical property change of a water absorbent resin (e.g., improvement of AAP and SFC and decrease of CRC) and also with the remaining amount of a surface-crosslinking agent; however, a surface-crosslinking agent is required to cause substantially no reaction in the mixing apparatus, and if reacted, it should be at highest 0 to 50%, desirably 0 to 10%, and particularly desirably 0 to 1% of the aimed reaction.

As a heating method, conventionally known heating means may properly be employed and heating may be carried out by circulating, for example, steam, warm water, hot air blow, other oil type heat medium, or a heating wire (plane) such as Nichrome wire in the stirring shaft, more preferably, in the inside of the stirring blades. During heating the stirring shaft, the heat medium or the heating wire may be communicated entirely or partially with the stirring shaft or the stirring blades, but preferably entirely. In addition, even in the case where the heat medium or the heating wire is communicated with only a part of the stirring shaft or the stirring blades, it is sufficient that the stirring shaft or the stirring blades are heated entirely to a prescribed temperature by conduction heating of the stirring shaft or the stirring blades.

In the present invention, the stirring shaft of a mixing apparatus is heated and it is preferable to heat also the inner wall of a mixing apparatus, that is, the inner face of the trunk of the mixing apparatus. Herein, the trunk of a mixing apparatus means a cylindrical portion of a mixing apparatus represented by a cylindrical vertical or transverse type mixing apparatus (e.g., shown in FIGS. 1, 3, and 4) and includes the column side face and upper and lower faces of the cylinder. The heating temperature of the inner wall is preferably 50° C. or higher, and its upper limit is 250° C., preferably 90 to 170° C., and more preferably 100 to 150° C. Heating is preferably carried out also for the side face (trunk portion) and its front and rear faces (faces in the front side and the rear side of the device in the moving direction of a water absorbent resin; e.g., the front and rear bottom faces in the case of a transverse installation type cylindrical device) of the inner wall of a mixing apparatus. Heating may be carried out for either a portion or the entire face of the trunk (e.g., column side face and upper and lower faces of a cylinder) and preferably for 50 to 100%, more preferably for 70 to 100%, still more preferably 90 to 100%, and particularly substantially 100% of the surface area. The heating means may be same as described above.

The pressure in the inside of the mixing apparatus may be normal pressure, increased pressure, or reduced pressure and in terms of accomplishment of the present invention, normal pressure or reduced pressure is preferable and reduced pressure is more preferable and reduced pressure state as described below is still more preferable.

(b) Temperature of Gas Current in Continuous Mixing Apparatus

Second means to be employed as a method for obtaining the effect of the present invention, in place of or in addition to the method for heating the stirring shaft of a mixing apparatus, is a method for operating a mixing apparatus in pressure reduced relative to the ambient pressure and controlling the temperature of a gas current in the mixing apparatus at that time to be at lowest 40° C. by circulating gas current, preferably air, in the mixing apparatus during mixing a surface-crosslinking agent.

Herein, "temperature of gas current" means the temperature in the space part in the inside of the mixing apparatus and substantially indicates the temperature near the outlet for a mixture of the mixing apparatus and is defined as gas temperature at the outlet. To solve the problems, in the present invention, the temperature of the gas current in a mixing apparatus is preferably 40 to 95° C., more preferably 45 to 90° C., and still more preferably 50 to 80° C. Herein, the gas may be air, an inert gas, steam, or their mixture, and preferably air.

In the case where the gas current is at lower than 40° C., the physical properties after surface-crosslinking (e.g., the water absorption against pressure represented by AAP, and liquid permeability represented by SFC and GBP) may possibly be deteriorated and become instable (e.g., increase of standard deviation) as in the above (a), and therefore, the effect of the present invention tends to be scarcely exerted.

As a method for heating the gas current, heated gas current may be introduced positively into a mixing apparatus from the outside, or according to the above (a), while the shaft or the inner wall of a mixing apparatus and also water absorbent resin particles to be introduced being heated, the gas current in the inside of the mixing apparatus may be heated by controlling the gas current coming in and going out the mixing apparatus to be in a prescribed amount and preferably keeping the inside of the mixing apparatus in reduced pressure. In addition, the temperature of the gas current cannot be definitely 40° C. by simply heating the inner wall (e.g., U.S. Pat. No. 6,576,713), it is naturally necessary to control the flow amount of the gas coming in the inlet and going out the outlet of a continuous mixing apparatus together with a water absorbent resin and further, the temperature of the gas current can be controlled by heating the stirring shaft and blades.

The temperature of a mixture (indispensably containing a water absorbent resin and a surface-crosslinking agent) from the mixing step of the surface-crosslinking agent to the surface-crosslinking step is preferably 50 to 95° C. and more preferably 55 to 90° C. In order to control the temperature of the gas current and a water absorbent resin, it is preferable to carry out the mixing at a speed so high as to control the average residence time of the water absorbent resin in the mixing apparatus to be higher than 0 second and within 3 minutes. The average residence time is more preferably within 1 minute and still more preferably within 0.5 minutes. If the temperature or the residence time is out of the range, the physical properties after surface-crosslinking may possibly be deteriorated.

A water absorbent resin with high physical properties can be continuously and stably obtained even at the time of scale-up to a large scale of 1 t/hr or more by controlling the temperature of the stirring shaft of a mixing apparatus or the temperature of the gas current as described above.

The reason for achieving the effect as described may supposedly be attributed to the following. In the production for a long duration, it is made possible to form a uniform coating on a base polymer with the surface-crosslinking agent by controlling the temperature of the stirring shaft of a mixing apparatus or the temperature of the gas current as described above. Therefore, a fine surface-crosslinking layer (few un-crosslinked parts) is formed even in the following surface-crosslinking step and as a result, a water absorbent resin with high physical properties can be continuously and stably obtained. Nevertheless, the present invention should not be limited to the above described presumption.

A conventional mixing apparatus for the surface-crosslinking is exemplified in the above-mentioned Patent Documents 1 to 41 and for example, U.S. Pat. No. 6,576,713 has disclosed a technique of using a stirring mixing apparatus with an inner wall temperature of 40° C. or higher in the mixing apparatus; however, any one of the techniques does not pay attention to heating of a shaft or blades or the temperature or pressure of the inside gas current, and does not imply the present invention at all.

(c) Surface Roughness of Continuous Mixing Apparatus

Figure 2:
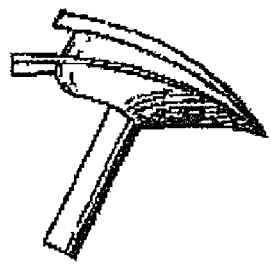
FIG. 2 is a schematic view showing a hoe-like stirring blade to be used in a hoe-type blender.

In the present invention, as a mixing apparatus for a surface-crosslinking agent, it is preferable to use a continuous, high rotating speed stirring type mixing apparatus, particularly a transverse type, continuous, high rotating speed stirring device (e.g., FIGS. 1, 3 and 4), and especially preferable to use a hoe type blender (e.g., FIGS. 1 and 2). It is also preferable that the inner face of a mixing apparatus (e.g., shown by the reference numeral 60 of FIG. 1 and the reference numeral 2 of FIG. 4) is made smooth and its surface roughness (Rz) is preferable to be controlled to 800 nm or lower. The surface roughness (Rz) is preferably 500 nm or lower, more preferably 300 nm or lower, particularly preferably 200 nm or lower, still more preferably 185 nm or lower, and most preferably 170 nm or lower. In the case where the surface roughness (Rz) does not satisfy the range, since the friction with the water absorbent resin particles becomes high and thus the physical properties may possibly be deteriorated. The surface roughness (Rz) means the maximum value (nm) of the highest height of the surface unevenness and defined in JIS B 0601-2001. The lower limit of the surface roughness (Rz) is 0 nm; however, it is not so much different in the case where it is about 10 nm, and thus about 20 nm is satisfactory. In terms of long time stability, the surface roughness is preferably controlled in the following metal face.

From a viewpoint described above, a portion or the entire body of the mixing apparatus may be made of a resin; however, it is preferable that 50 to 100%, more specifically 80 to 100%, and most specifically 100% of the inner face (the inner wall and the inner face of the shaft, blades, etc.) of the mixing apparatus is made of a metal, preferably stainless steel. mixing apparatuses having inner walls with resin coatings as disclosed in the above-mentioned US Patent Document No. 26 (U.S. Pat. No. 5,140,076) and US Patent Document No. 28 (US Patent Laid-Open No. 2004/240316) are known; however, in the case of such a resin coating, deterioration of the surface-crosslinking physical properties is sometimes observed due to a long time operation and thus it may sometimes result in fluctuation of the physical properties (increase of the standard deviation). That is, a technique of preventing the deposition by a resin (particularly of Teflon (polytetrafluoroethylene) coating) in the inner face of a mixing apparatus is also known as disclosed in Patent Documents 26 and 28; however, the resin is peeled off during a long time operation for several months or several years and accordingly, the deposition of a water absorbent resin in the inside of the mixing apparatus is caused and the physical properties (e.g., AAP/SFC) are gradually deteriorated for a long time operation. Periodical re-coating of the inner face of the mixing apparatus with a resin for dealing with the peeling of the resin is accompanied with stoppage of production for a long period; however, the present invention is free from this problem.

A material is preferably a metal, more preferably a stainless steel in terms of the heat transmission of the above-mentioned heat medium, and preferably finished by mirror-finishing. The mirror-finishing suppresses damages on the water absorbent resin particles. The damage suppression effect is further improved by mirror-finishing of a stainless steel. Examples of the stainless steel include SUS 304, SUS 316, and SUS 316L. The surface roughness (Ra) other than the surface roughness (Rz) is also defined according to JIS B0601-2001 and a preferable value thereof is also the same as that of the surface roughness (Rz). The surface roughness (Ra) is preferably 250 nm or lower and more preferably 200 nm or lower. These surface roughness values may be measured according to JIS B 0651-2001 by a probe type surface roughness meter. The surface roughness can be applied not only for the heating apparatus but also for apparatuses before and after the heating apparatus, preferably, for a cooling apparatus, a transportation pipe (particularly, a pneumatic transportation pipe) and a hopper, and the effect of improving physical properties by surface-crosslinking can be heightened.

(d) Operation Condition of Continuous Mixing Apparatus

Stirring is carried out at 100 to 10000 rpm and more preferably at 300 to 2000 rpm and the residence time is within 180 seconds, more preferably 0.1 to 60 seconds, and still more preferably about 1 to 30 seconds.

It is also preferable to keep the inside of the mixing apparatus in slightly reduced pressure. "Pressure-reduced state" means the barometric pressure kept lower than atmospheric pressure. In addition, "pressure reduction degree relative to atmospheric pressure" means the pressure difference from the atmospheric pressure and is denoted as a positive (plus) value in the case where the barometric pressure is lower than the atmospheric pressure. For example, in the case where the atmospheric pressure is standard atmospheric pressure (101.3 kPa), "pressure reduction degree is 10 kPa" means the barometric pressure is 91.3 kPa. In this application, "pressure reduction degree relative to atmospheric pressure" may be referred to simply also as "pressure reduction degree". In the case where pressure is not reduced, a water absorbent resin powder may possibly flow over an air intake port of a mixing apparatus and it is thus not preferable. Dust (ultrafine particles of the water absorbent resin and inorganic fine particles used based on the necessity) can be removed from a water absorbent resin by slightly reducing the pressure and thus it is preferably in terms of decrease of dust.

In terms of improvement of the above-mentioned effect due to pressure reduction, the lower limit of the pressure reduction degree is preferably higher than 0 kPa, more preferably 0.01 kPa or higher, and still more preferably 0.05 kPa or higher. Excess pressure reduction may possibly remove even a necessary water absorbent resin powder besides dust to the outside of the device and it may possibly result in decrease of yield. Additionally, in terms of suppression of leap of a powder in the system and also in terms of suppression of excess cost for a gas discharge device, the pressure reduction degree is preferably 10 kPa or lower, more preferably 8 kPa or lower, still more preferably 5 kPa or lower, and still more preferably 2 kPa or lower. A preferable numeral range of the pressure reduction degree may be selected arbitrarily between the above-mentioned lower limit and upper limit.

In the present invention, the temperature of the mixture is preferable to be increased by 0.5° C. or more by continuously mixing a surface-crosslinking agent with the dried water absorbent resin powder. That is, in the step of adding a surface-crosslinking agent and water to the mixing apparatus, the temperature of the obtained water absorbent resin mixture (generally, a mixture obtained by mixing 0.001 to 10 parts by mass of a surface-crosslinking agent and 0.5 to 10 parts by mass of water to 100 parts by mass of the particulate water absorbent resin) is preferable to be increased higher by 0.5° C. or more than the temperature of the particulate water absorbent resin (before mixing). The temperature increase is more preferably by 2° C. or more, still more preferably 3 to 60° C., particularly preferably 4 to 50° C., and most preferably 6 to 30° C.

This temperature control can be carried out by controlling the shaft heating temperature, the temperature of the inner wall of the mixing apparatus, or the residence time of the mixture in the mixing apparatus. It is preferable to control the temperature increase range as described above by adjusting the temperature of the inner wall of the mixing apparatus by using steam or the like. The temperature of the water absorbent resin mixture taken out of the mixing apparatus is preferably 50 to 140° C., still more preferably 60 to 110° C., and particularly preferably 70 to 95° C.

In the step of adding a surface-crosslinking agent and water to the mixing apparatus, it is supposed that penetration and diffusion of the surface-crosslinking agent in the water absorbent resin surface is optimized by increasing the temperature of the water absorbent resin mixture. As a result, as compared with conventional techniques, the present invention can provide excellent physical properties and in addition to that, the present invention is advantageous in a point that the present invention can shorten the reaction time and save the energy.

In the surface-crosslinking step following the mixing step of the surface-crosslinking agent, a suitable condition for continuously and stably obtaining a water absorbent resin with high physical properties will be described as follows.

(e) Surface-Crosslinking Agent

The present invention further includes a surface-crosslinking step after drying. The production method of the present invention is preferably applicable for a method for producing a water absorbent resin with high absorption against pressure (AAP) and liquid permeability (SFC) and continuous manufacture in a huge scale (particularly 1 t/hr), and particularly preferably applicable for high temperature surface-crosslinking of a water absorbent resin.

Treatment agents described in Patent Documents 1 to 19, particularly surface-crosslinking agents, are used for the surface treatment in the present invention. From the viewpoints of physical properties at the time of scale-up, covalent bonding surface-crosslinking agents are used among them, and preferably covalent bonding surface-crosslinking agents and ion bonding surface-crosslinking agents are used in combination.

(Covalent Bonding Surface-Crosslinking Agent)

Examples of a surface crosslinking agent to be employed in the present invention may include various organic or inorganic crosslinking agents, and organic surface crosslinking agents are preferably used. From the viewpoints of physical properties of obtained water absorbent resin, preferable examples to be used as the surface crosslinking agent are polyhydric alcohol compounds, epoxy compounds, polyamine compounds and their condensation products with haloepoxy compounds, oxazoline compounds (mono-, di-, or poly-)oxazolidinone compounds, and alkylene carbonate compounds. Particularly dehydration reactive crosslinking agents containing polyalcohol compounds, alkylene carbonate compounds, and oxazolidinone compounds, which require a high temperature reaction, are usable. In the case where no dehydration reactive crosslinking agent is used, the physical properties may sometimes be inferior or the difference of the effects of the present invention may sometimes be hard to be caused in some cases.

More concretely, examples are compounds exemplified in U.S. Pat. Nos. 6,228,930, 6,071,976, and 6,254,990. Examples are polyalcohol compounds such as mono-, di-, tri-, or tetra-propylene glycol, 1,3-propanediol, glycerin, 1,4-butanediol, 1,3-butanediol, 1,5-pentanediol, 1,6-hexanediol, sorbitol, etc.; epoxy compounds such as ethylene glycol diglycidyl ether, glycidol, etc.; alkylene carbonate compounds such as ethylene carbonate; oxetane compounds; and cyclic urea compounds such as 2-imidazolidinone.

(Ion-Bonding Surface Crosslinking Agent)

Further, other than the above-mentioned organic surface crosslinking agent, an ion-bonding inorganic surface crosslinking agent (crosslinking agent derived from polyvalent metal) may be used to improve the liquid permeability potential or the like. Examples usable as the inorganic surface crosslinking agent may include divalent or higher, preferably, trivalent to tetravalent polyvalent metal salts (organic salts and inorganic salts) and hydroxides. Polyvalent metals to be used are aluminum, zirconium, etc., and aluminum lactate and aluminum sulfate are usable. These inorganic surface crosslinking agents may be used simultaneously with or separately from the organic surface crosslinking agent. The surface crosslinking with polyvalent metals is exemplified in International Publication Nos. 2007/121037, 2008/09843, and 2008/09842, in U.S. Pat. Nos. 7,157,141, 6,605,673, and 6,620,889, in US Patent Application Publication Nos. 2005/0288182, 2005/0070671, 2007/0106013, and 2006/0073969.

Further, other than the above-mentioned organic surface crosslinking agent, a polyamine polymer, particularly, having a mass average molecular weight of about 5000 to 1000000 may be used simultaneously or separately to improve the liquid permeability potential and the like. Usable polyamine polymers are exemplified in U.S. Pat. No. 7,098,284, International Publication Nos. 2006/082188, 2006/082189, 2006/082197, 2006/111402, 2006/111403, and 2006/111404 etc.

(The Used Amount)

The use amount of the surface crosslinking agent is preferably 0.001 to 10 parts by mass and more preferably 0.01 to 5 parts by mass relative to 100 parts by mass of the water absorbent resin particle. Water can be preferably used in combination with the surface crosslinking agent. The amount of water to be used is preferably in a range of 0.5 to 20 parts by mass and more preferably 0.5 to 10 parts by mass relative to 100 parts by mass of the water absorbent resin particle. In the case of using the inorganic surface cross-linking agent and the organic surface crosslinking agent in combination, the agents are used preferably in a range of 0.001 to 10 parts by mass and more preferably 0.01 to 5 parts by mass, respectively.

Further, at that time, a hydrophilic organic solvent may be used and its amount is in a range of 0 to 10 parts by mass and preferably 0 to 5 parts by mass relative to 100 parts by mass of the water absorbent resin particle. Still more, at the time of mixing a cross-linking agent solution with the water absorbent resin particles, a water insoluble fine particle powder, and a surfactant may coexist to an extent that the effect of the present invention is not hindered, that is, in a range, for example, of 0 to 10 parts by mass, preferably 0 to 5 parts by mass, and more preferably 0 to 1 part by mass. The surfactant to be used and its use amount are exemplified in U.S. Pat. No. 7,473,739 etc.

(f) Temperature of Water Absorbent Resin Before Surface-Crosslinking

In the present invention, the temperature of water absorbent resin particles (e.g., a water absorbent resin in which it is mixed with the surface-crosslinking agent and then before it is introduced into the surface-crosslinking step; the resin is also referred to as a particulate water absorbent agent) to be supplied to the surface-crosslinking step or to a transportation tube is preferably 30° C. or higher, more preferably 40° C. or higher, and still more preferably 50° C. or higher. The upper limit thereof is preferably 100° C. and more preferably 95° C. Deterioration of the physical properties of the water absorbent resin particles (particulate water absorbent agent) can be suppressed by keeping the temperature of the particulate water absorbent resin to be supplied to a transportation tube at a prescribed temperature or higher. Specifically, a significant effect is caused on maintain of the physical properties such as saline flow conductivity (SFC).

(5-2) Heat Treatment Step

While covering or being absorbed in the surface of a water absorbent resin mixed with the surface-crosslinking agent, the surface-crosslinking agent exists unevenly in the surface. The obtained mixture (the water absorbent resin and the surface-crosslinking agent) is subjected to crosslinking reaction in a reaction step. The reaction may be carried out by active energy beam such as ultraviolet rays and at room temperature; however, heat reaction is preferable. Particularly, in the case of obtaining a sanitary material (particularly, paper diaper), the water absorption against pressure (AAP) described below can be improved to be in a range as described below, preferably 20 g/g or higher, and more preferably about 23 to 30 g/g by the surface-crosslinking.

A heating device to be used in the present invention is preferably continuous type ones and examples include a groove mixing and drying device, a rotary drier, a disc drier, a fluidized bed drier, a flash drier, an infrared drier, a paddle type drier, a vibrating and fluidizing drier. The heating temperature is 70 to 300° C., preferably 120 to 250° C., and more preferably 150 to 250° C. and the heating time is preferably in a range of 1 minute to 2 hours.

Figure 5:
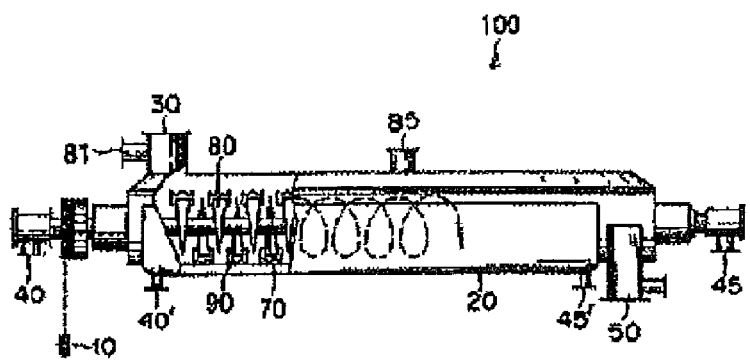
FIG. 5 is a schematic view showing one example of a biaxial heating device (reaction device) to be used after mixing of a surface-crosslinking agent.

Among these heating devices, in terms of physical property improvement and stability, a transverse type continuous stirring device represented by a paddle-type drying device (e.g., FIG. 5) is preferable and a (transverse type) continuous stirring device showing a stirring power index (a) as described below is particularly suitably usable. It is also preferable that the mixing apparatus and the heating device are connected and periodically shielded (b) from each other.

Hereinafter, conditions to be employed preferably in the present invention will be described.

(a) Structure of Heating Device (Stirring Power Index)

The stirring power index found in the present invention is defined as the following expression. A water absorbent resin with high physical properties can be continuously and stably obtained even at the time of scale-up to a large scale (particularly, 1 t/hr or more) based on a specified apparatus and specified parameters thereof (stirring power index).

The stirring power index is defined as (stirring power index)=((power consumption of apparatus at the time of surface treatment)−(power consumption at the time of idling)×average retention time)/ (treatment amount per unit time×average retention time)

The stirring power index can be easily calculated as described above from the power consumption of apparatus at the time of surface treatment and the power consumption at the time of idling. If this stirring power index exceeds 15 W·hr/kg, the physical properties (particularly, liquid permeability) are deteriorated and on the other hand, if it is under 3 W·hr/kg, the physical properties (particularly, water absorption against pressure) are also deteriorated. The stirring power index is more preferably in a range of 4 to 13 W·hr/kg, still more preferably 5 to 11 W·hr/kg, particularly preferably 5 to 10 W·hr/kg, and most preferably 5 to 9 W·hr/kg.

The control of the stirring power index can be determined properly in consideration of adjustment of the supply amount and discharge amount of the water absorbent resin, the particle size or bulk specific gravity of the water absorbent resin, the rotation speed and shape of the apparatus, the composition of the surface treatment agent, and the retention time, and the followings are preferable conditions.

An apparatus to be used in the present invention is preferably a continuous type apparatus and examples thereof include a groove type mixing and drying apparatus, a rotary drier, a disk drier, a fluidized bed drier, a flash drier, an infrared drier, a paddle drier, and a vibrating and fluidizing drier. From the viewpoints of improvement of physical properties and stabilization, a paddle drier is preferable. If an apparatus is used other than above mentioned preferable apparatus, physical properties obtained at the time of scale-up to a larger scale and continuous production process might be degraded.

Hereinafter, preferable surface treatment method and stirring power index control method will be described.

(Inclined Angle)

Heat treatment is carried out for the water absorbent resin after the surface treatment agent is added to the stirring apparatus. The transverse type continuous stirring apparatus is a necessary apparatus. In terms of control of the stirring power index, the transverse type continuous stirring apparatus is preferable to have a downward inclined angle of 0.1 to 10°. The inclined angle is more preferably 0.5 to 5° and still more preferably 1 to 4°. In the case where the inclined angle does not satisfy the range of 0.1 to 10°, the physical properties may possibly be deteriorated in some cases due to process damage.

(Aspect Ratio)

The aspect ratio (length of apparatus in movement direction/width of apparatus of cross section to movement direction) of the transverse type continuous stirring apparatus is preferably 1 to 20. The aspect ratio is more preferably 1.5 to 10 and still more preferably 2 to 5. The aspect ratio is determined as the ratio of the vertical (movement direction) length and the transverse (perpendicular to the movement direction in a plane) length in the inside of the apparatus. In the case where the aspect ratio does not satisfy the range, the physical properties may possibly be deteriorated in some cases due to process damage. or the piston flow property in the apparatus may be sometimes worsened and the stability of the performance may be worsened in some cases.

(Scraping Blades)

Figure 6:
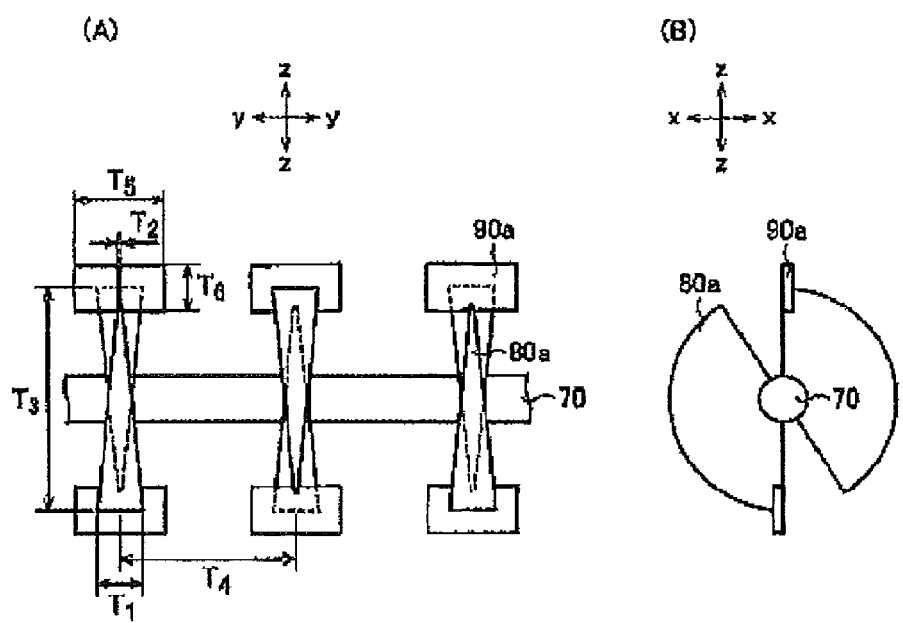
FIG. 6 is a schematic view of a scraping blade of a biaxial heating device.

The transverse type continuous stirring apparatus is preferable to have scraping blades (the scraping blades are denoted, for example, by 90a in FIG. 6). The scraping blades are described in Patent Document 31 (JP-A No. 2004-352941). If the scraping blades are used, the stirring power index can be controlled to be low and as a result, the physical properties of the water absorbent resin can be improved.

(Average Retention Time)

In terms of process damage, the average retention time of the water absorbent resin is preferably controlled to be 0.05 to 2 hours. The average retention time is more preferably 0.1 to 1 hour and still more preferably 0.2 to 0.8 hours.

The average retention time measurement for the water absorbent resin in the transverse type continuous stirring apparatus of the present invention will be described. The retention time in the apparatus (also known as heating time or reaction time in the transverse type continuous stirring apparatus) is controlled by various factors such as effective volume of the apparatus (in the case where there is a stirring shaft arranged in the transverse direction, the effective volume refers to the volume covering the upper most surface of a stirring disk as the apex), the amount of the water absorbent resin particles to be supplied, inclined angle, the rotation speed of the stirring shaft, the shape of the scraping blade, the bulk specific gravity of the water absorbent resin particles, the kind of the surface treatment agent, the height of the discharge bank installed in the discharge outlet of the transverse type continuous stirring apparatus. These factors considerably affect not only the retention time but also the stirring power index. A method of measuring the average retention time is carried out by actually operating the apparatus under the condition in which the various factors are fixed and measuring the mass of the water absorbent resin particles remaining in the apparatus after stopping the operation of the apparatus. Alternatively, the average retention time can also be determined by unsteadily introducing a substance easy to be identified (for example, a compound containing sulfur) into the charging inlet of the apparatus as a tracer substance, tracing the concentration fluctuation of the substance at the discharge outlet, obtaining the retention time distribution function, and carrying out calculation according to the retention time distribution function. As the tracer substance, for example, a water-soluble sulfuric acid salt can be used. Further, as a concentration analysis method, there is a method of tracing the concentration fluctuation by measuring the intensity ratio of the characteristic x-ray of sulfur and a monovalent cation (e.g., sodium) with EPMA, XMA, or the like in the case of a partially neutralized polyacrylic acid water absorbent resin. The retention time distribution function and the average retention time are described in detail in "Introduction of Chemical Reaction Engineering (Hannou Kogaku Gairon)", Hiroshi KUBOTA, issued by the Nikkan Kogyo Shimbun, Ltd.

(Rotary Shaft and Stirring Disk)

The transverse type continuous stirring apparatus has one or a plurality of rotary shafts, preferably 2 to 10 rotary shafts, and particularly 2 shafts. Further, the number of a stirring disk (e.g., in FIG. 2) or a stirring blade may be determined properly in accordance with the size (capacity) of the apparatus, and it is preferably 2 to 100 disks and more preferably 5 to 50 disks per one shaft.

(Periodical Shielding)

In terms of physical property stability and improvement by surface-crosslinking, it is conducted to periodically shield the rotation stirring type mixing apparatus and the transverse type stirring apparatus after the water absorbent resin and the surface treatment agent solution are mixed to be introduced into the stirring apparatus. The interval for the periodical shielding is preferably 0.001 to 5 minutes, more preferably 0.005 to 1 minute, still more preferably 0.01 to 0.1 minutes, and particularly preferably 0.01 to 0.05 minutes. Execution of the periodical shielding makes it possible to carry out periodic introduction of the water absorbent resin into the continuous apparatus installed downstream (introduction of the water absorbent resin into a heating apparatus from a mixing apparatus or into a cooling apparatus from a heating apparatus); that is, the introduction is turned on and off intermittently. In the case where no periodic shielding is carried out in the surface-crosslinking step, the physical properties of a water absorbent resin to be obtained may possibly be deteriorated in some cases. The shielding ratio (the ratio of the time when the water absorbent resin is shielded from the continuous apparatus installed downstream) is preferably in a arrange of 1 to 80%, more preferably 2 to 40%, still more preferably 5 to 30%, particularly preferably 5 to 20%, and most preferably 5 to 10%, in terms of stabilization of the physical properties (standard deviation). It is sufficient that the water absorbent resin in the above amount range (e.g., 1 t/hr or more) is fed to a next apparatus even if the periodical shielding is executed. For example, in the case of a rotary valve, the shielding interval is defined as the reciprocal number (minute) of the rotation speed (rpm), and the shielding ratio is defined as a value calculated by dividing the theoretical rotation speed (rpm) per one minute of the rotary valve needed for discharging a mixture (wet powder; a mixture of the water absorbent resin and the surface-crosslinking agent solution) to be supplied to the continuous high speed mixing apparatus (theoretical rotation speed is obtained from the volume flow rate calculated from the volume per one rotation of the rotary valve, the mass flow rate of the mixture to be discharged, and the bulk specific gravity) by actual rotation speed (rpm) of the rotary valve, and multiplying the calculated value by 100. The shielding ratio is specifically defined as a value calculated by dividing the rotation speed (rpm) per one minute of the rotary valve needed for discharging a wet powder (a mixture of the water absorbent resin and the surface-crosslinking agent) out of a mixing apparatus per unit time by the actual rotation speed of the rotary valve. It is calculated, for example, in the case of the example of the present invention as $[1500\times(1+3.5/100)/0.47/1000/0.02/60/25]\times100=11.0\%$.

The amount of the water absorbent resin retained by periodical shielding is preferably 0 to 2 mass % and more preferably exceeding 0 and to 1 mass % relative to the treatment amount. The volume per one rotation of the rotary valve may be determined properly and it is preferably 0.1 to 0.001 [$m^3$/lev (one rotation)], more preferably 0.2 to 0.002 [$m^3$/lev], and still more preferably 0.1 to 0.01 [$m^3$/lev]. In the case where the periodic shielding is carried out or even when the periodic shielding is no carried out, when the continuous apparatuses (the mixing apparatus, the heating apparatus, and the cooling apparatus if necessary) are connected, the distance from the outlet of an upstream apparatus and the inlet of an apparatus installed downstream is preferably 10 m or shorter. The distance is more preferably 5 m or shorter, still more preferably 3 m or shorter, and particularly preferably 2 m or shorter. At the time of connecting these apparatuses, the apparatuses are connected up and down; that is, the downstream apparatus is connected to a lower side of the upstream apparatus. A shielding apparatus of the water absorbent resin particles may be installed between the upstream apparatus and the downstream apparatus. The lower limit of the distance may be determined properly in accordance with the sizes of the apparatuses or in a range in which a shielding apparatus described below can be housed. In the case where the distance is too large or the apparatuses are not connected up and down, the physical properties of a water absorbent resin to be obtained may possibly be deteriorated in some cases. In the case of connecting up and down, the mixing apparatus, the heating apparatus, and the cooling apparatus if necessary may be connected up and down in this order. Connecting of the cooling apparatus may be above or beside the heating apparatus.

A gate, a valve, a damper, a rotary feeder, a table feeder, or the like is installed as a periodically shielding apparatus in a connecting part of the continuous apparatuses so that the periodical shielding can be carried out. Examples of the gate to be employed include a slide gate, a roller gate, a tainter gate, a radial gate, a flap gate, a rolling gate, and a rubber gate. Examples of the valve to be employed include a Howell-Bunger (fixed cone dispersion) valve, a hollow jet valve (a movable cone dispersion valve), a jet flow valve, a butterfly valve, a gate valve (a partition valve), an orifice valve, a rotary valve (a valve for opening or closing by rotating a cylinder), and a Johnson valve (a valve for opening or closing by moving a conical valve body back and forth). These shielding apparatuses may be installed in an outlet of the mixing apparatus, or in an inlet of the heating apparatus, or in a middle part thereof after the outlet of the mixing apparatus (e.g., FIG. 1, FIG. 2, and FIG. 4) and the inlet of the heating apparatus (e.g., FIG. 5) are connected. Also, the periodic shielding is similarly carried out preferably at an outlet of the heating apparatus. Specifically, the periodic shielding is similarly carried out preferably between an outlet of the heating apparatus (e.g., FIG. 1) and the cooling apparatus. The shielding and connecting of the apparatuses are preferably carried out via a valve, particularly a rotary valve, among these shielding apparatuses. The size (it refers to diameter: however, in the case where the cross section is other than a circular shape, it is converted into the diameter of a circle with the same surface area) of the valve may be selected properly and it is preferably, for example, 1 to 100 cm in diameter and more preferably 10 to 50 cm in diameter.

Each shielding apparatus is operated at less than 100% of the maximum treatment amount (kg/hr; the maximum amount of a substance which can be passed through the shielding apparatus per unit time). The operation condition is preferably 5 to 95%, more preferably 10 to 90%, and still more preferably 20 to 80%. In the case where the operation condition of the shielding apparatus is out of the above-mentioned range, the physical properties of a water absorbent resin to be obtained may possibly be deteriorated in some cases and the performance may possibly become unstable. In the case where a rotary shielding apparatus such as a rotary valve is used, the rotation speed thereof may be determined properly and it is preferably 1 to 500 rpm (rotation/minute). The rotation speed is more preferably 5 to 200 rpm, still more preferably 10 to 100 rpm, and particularly preferably 20 to 100 rpm. The maximum treatment performance of the shielding apparatus may be determined properly and it is, for example, preferably 0.01 to 20 t/hr and more preferably 0.1 to 5 t/hr.

(b) Operation Condition of Heating Apparatus (Filling Ratio)

It is preferable to continuously supply the water absorbent resin in such a manner that the filling ratio (volume ratio) of the transverse type continuous stirring apparatus with the water absorbent resin can be 50 to 90%. The filling ratio is more preferably 55 to 85% and still more preferably 60 to 80%. In the case where the filling ratio does not satisfy the above-mentioned range, the stirring power index is hard to be controlled, and the physical properties of a water absorbent resin to be obtained may possibly be deteriorated in some cases. The position at 100% filling ratio is the apex part of a stirring disk of a rotary shaft as described above.

It is preferable to continuously supply the water absorbent resin in such a manner that the mass surface area ratio of the water absorbent resin in the transverse type continuous stirring apparatus can be 100 kg/m$^2$/hr or lower. It is more preferably 90 kg/m$^2$/hr or lower and still more preferably 50 to 70 kg/m$^2$/hr. In the case where the mass surface area ratio does not satisfy the above-mentioned range, the stirring power index is hard to be controlled and the physical properties of a water absorbent resin to be obtained may possibly be deteriorated in some cases.

Herein, the mass surface area ratio is defined by the following equation.

$$\text{(Mass surface area ratio)} = \text{(Mass flow rate of water absorbent resin per unit time)}/\text{(Heat transfer area of apparatus)}$$

In the case where the jacket surface of an apparatus trough is only for heat insulation, the mass surface area ratio is defined as follows.

$$\text{(Mass surface area ratio)} = \text{(Mass flow rate of water absorbent resin per unit time)}/\text{(Heat transfer area of stirring shaft and stirring disk of apparatus)}$$

(Rotation Speed and Reaction Time)

According to the present invention, uniform heating and mixing can be carried out by adjusting the stirring speed of the transverse type continuous stirring apparatus to 2 to 40 rpm. If it is lower than 2 rpm, the stirring becomes insufficient and on the other hand, if it is higher than 40 rpm, a fine powder tends to be generated easily in some cases. The stirring speed is more preferably 5 to 30 rpm. The retention time in the apparatus is, for example, 10 to 180 minutes and more preferably 20 to 120 minutes. If it is shorter than 10 minutes, the crosslinking reaction tends to be insufficient. On the other hand, if it exceeds 180 minutes, the water absorption performance may possibly be deteriorated in some cases.

(Pressure Reduction)

In the present invention, it is preferable to set the inside of the transverse type continuous stirring apparatus to slightly reduced pressure. "Pressure-reduced state" means barometric pressure lower than atmospheric pressure. In addition, "degree of pressure reduction relative to atmospheric pressure" means the pressure difference with the atmospheric pressure and is denoted as a positive (plus) value in the case where barometric pressure is lower than atmospheric pressure. For example, in the case where atmospheric pressure is standard atmospheric pressure (101.3 kPa), the expression that "degree of pressure reduction is 10 kPa" means that barometric pressure is 91.3 kPa. In this application, "degree of pressure reduction relative to atmospheric pressure" may also be referred to simply as "degree of pressure reduction". In the case where pressure is not reduced, a water absorbent resin powder may possibly flow over the air intake port of the mixing apparatus and it is thus not preferable. Dust (ultrafine particles of the water absorbent resin or inorganic fine particles used if necessary) is removed from the water absorbent resin by slightly reducing the pressure and thus it is also preferable in terms of a decrease in dust.

From the viewpoint of improvement of the effect attributed to pressure reduction, the lower limit of the degree of pressure reduction is preferably higher than 0 kPa, more preferably 0.01 kPa or higher, and still more preferably 0.05 kPa or higher. Excess pressure reduction may possibly remove even a necessary water absorbent resin powder besides dust to the outside of the apparatus and it may possibly result in a decrease in yield. Additionally, from the viewpoints of suppression of leap of a powder in the system and of suppression of excess cost for the exhaust system, the degree of pressure reduction is preferably 10 kPa or lower, more preferably 8 kPa or lower, still more preferably 5 kPa or lower, and particularly preferably 2 kPa or lower. The preferable numeral range of the degree of pressure reduction may be selected arbitrarily between the lower limit and the upper limit.

(Atmosphere)

The atmosphere in the transverse type continuous stirring apparatus may be air, or an inert gas such as nitrogen for prevention of coloration or prevention of combustion, and steam may be added properly. The temperature and the dew point are determined properly, and the atmospheric temperature (defined as the gas temperature in the upper part space of the apparatus) is preferably 30 to 200° C. and more preferably 50 to 150° C. The dew point is preferably 0 to 100° C. and more preferably 10 to 80° C.

(5-3) Cooling Step

Cooling step can be conducted after heat treatment step as needed. In the case where dehydration reactive crosslinking agent(s) such as polyalcohol compounds, alkylene carbonate compounds, and oxazolidinone compounds, which require a high temperature reaction, is/are used, it is preferable to conduct cooling step.

An apparatus to be used for cooling is not particularly limited. Already mentioned transverse type continuous stirring apparatus for the heat treatment can be used. Also an apparatus exemplified in the above mentioned patent document 41 (U.S. Pat. No. 7,378,453), for example a stirring dryer having 2 rotary shafts having cooling water is flow inside an inner wall and/or other heat transfer surface. The cooling water temperature is controlled to less than the heating temperature at surface treatment step and preferable cooling water temperature is 25° C. or more and less than 80° C. In the present invention, surface treat reaction by heating can be controlled with the cooling apparatus which is conducted as needed, thereby physical properties of the water absorbent resin can be improved. An apparatus having mechanical stirring (which can be combined with stirring by airflow) as exemplified in patent document 41 or an apparatus which can stir and mix by combining vibrating stirring and airflow stirring is preferably used as the cooling apparatus. Herein, the periodic shielding is carried out preferably at an inlet of the cooling apparatus (which is connected with outlet of the above mentioned heating apparatus), and further preferably at an outlet of the cooling apparatus.

The cooling step is carried out preferably in the transverse type continuous stirring apparatus as mentioned above. The cooling is carried out while adjusting the stirring power index of the transverse type continuous stirring apparatus to preferably 3 to 15 W·hr/kg. The stirring power index is more preferably in a range of 4 to 13 W·hr/kg, still more preferably 5 to 11 W·hr/kg, particularly preferably 5 to 10 W·hr/kg, and most preferably 5 to 9 W·hr/kg. Abovementioned pressure reduction can be carried out as conducted in heat treatment step and preferably periodical shielding can be carried out as conducted in heat treatment step. The stirring power index (4 to 13 W·hr/kg, more preferably 5 to 11 W·hr/kg, particularly preferably 5 to 10 W·hr/kg, and most preferably 5 to 9 W·hr/kg) of the heating apparatus described above (also known as heat treatment apparatus, heater) may be the same or different from that of the cooling apparatus; however, in terms of physical properties, the stirring power index of the cooling apparatus (also known as chiller) is preferable to be smaller. The stirring power index of the cooling apparatus is preferably in a range of 0.99 to 0.25 times, more preferably 0.95 to 0.50 times, and particularly preferably 0.90 to 0.55 times as high as that of the heating apparatus.

(5-4) Others (a) Number of Surface Treatment Apparatuses

In terms of improvement of the stirring power index and physical properties, the polymerization step may be carried out preferably by continuous belt polymerization or continuous kneader polymerization and a plurality of surface treatment steps are preferably carried out in parallel for the polymerization step.

In the production method of the present invention, in terms of improvement of physical properties and stabilization, the surface-crosslinking step is carried out in 2 or more lines for 1 line of the polymerization step. The 1 line in the present invention means one system in which steps proceed from a raw material (monomer) until when a polymer gel, a water absorbent resin (including a recovered fine powder product), a particulate water absorbent agent and a final product are obtained. In the case where the system is branched into two, it is referred to as "2 lines". In other words, "2 or more lines" means a mode in which two or more apparatuses are arranged in parallel and operated simultaneously or alternately in a single step.

In the present invention, in the case where the respective steps are carried out in 2 or more lines, the upper limit for each step is about 10 lines, especially preferably 2 to 4 lines, still more preferably 2 to 3 lines, and particularly preferably 2 lines. The physical properties of a water absorbent resin to be obtained are improved by adjusting the number of the lines within the above range. From a viewpoint that in the case where the number of lines (divisions) is large, no dividing effect is caused, and the operation becomes complicated, and also it is not economical in terms of the cost, it is particularly preferable to simultaneously operate 2 lines, that is, 2 or more of the same apparatuses (particularly two apparatuses) in parallel.

In the present invention, the polymer gel or the water absorbent resin, which is a dried product of the polymer gel, is divided into 2 or more lines in the steps after the drying step, and the ratio of amounts divided may be determined for every step without any particular limitation. For example, in the case of dividing into 2 lines, the ratio is preferably 4:6 to 6:4, more preferably 4.5:5.5 to 5.5:4.5, still more preferably 4.8:5.2 to 5.2:4.8, and most preferably 5:5. Even in the case of dividing into 3 or more lines, it is preferable that the ratio of the maximum amount and the minimum amount of n divided portions is within the above range. The dividing operation may be carried out in a continuous manner or in a batch manner and the ratio of amounts divided is defined in accordance with the average amounts for a prescribed time.

In the present invention, the number of lines in the surface-crosslinking step is not particularly limited and the number thereof may be selected arbitrarily; however, in consideration of the construction cost and running cost of a plant etc, 1 line or 2 lines are preferable and 2 lines are particularly preferable. That is, in terms of physical properties, it is most preferable that the surface-crosslinking step and preferably further the crushing step and the classification step all have 2 or more lines (the upper limit is within the above range) for 1 line of the polymerization step.

In addition, in the case where a plurality of apparatuses are installed in parallel in place of one apparatus in the present invention, the apparatuses in parallel may properly be miniaturized. Even if the treatment capacity of the apparatus is miniaturized into ½, the cost of the apparatus is not lowered to a half; however, in the present invention, installation of specified apparatuses in parallel improves the physical properties of an absorbent agent to be obtained and decreases the ratio of the product out of the specification and it is thus found that it consequently results in a decrease in cost.

US Patent Application Publication No. 2008/0227932 discloses a technique of carrying out "polymerization in 2 lines" and the latter half in one line; Patent Document 30 (US Patent Application Publication No. 2007/149760) discloses a technique of "connecting in series" of a stirring and drying apparatus and a heating apparatus for surface-crosslinking; and WO 2009/001954 discloses a technique of "connecting in series" of belt polymerization apparatuses. In contrast, in the present invention, the physical properties are improved and stabilization is accomplished more than before by "arranging (substantially the same) apparatuses in parallel" in the specified step after completion of the polymerization step for one polymerization apparatus.

(Dividing Means)

In order to carry out surface-crosslinking in 2 or more lines in the present invention, a dividing step is included, and a dividing step of a particulate hydrous gel or a particulate water absorbent resin, which is a dried product of the gel, is preferably included, and a dividing step of a particulate water absorbent resin is more preferably included.

A dividing method to be employed may be, for example, the following means (a-1) to (a-3) for the particulate water absorbent resin after drying.

(a-1) A method for dividing the particulate water absorbent resin after storage in a hopper. Preferably, a quantitative feeder for a powder is used. As the quantitative feeder, a cycle feeder or a screw feeder is used suitably.

(a-2) A method for dividing the particulate water absorbent resin during the time of pneumatic transportation to a plurality of hoppers.

(a-3) A method for dividing the particulate water absorbent resin at the time of dropping (e.g., free fall). In this case, a riffle divider, a 3-way divider, or the like having hills and dams are used for the dividing. Additionally, a JIS sample reducing and dividing apparatus (riffle divider) has a structure partitioned into a large number of small chambers in which a fed sample is distributed alternately to two directions.

A dividing method to be employed for the polymer gel after polymerization may be, for example, the following means (a-4) to (a-6) or the combination thereof, and the polymer gel is supplied to the drying step in parallel.

(a-4) A method for dividing the particulate hydrous gel obtained by a kneader or a meat chopper at the time of dropping (e.g., free fall). For the dividing, a riffle divider, a 3-way divider, or the like having hills and dams are used in the outlet of the kneader or the meat chopper.

(a-5) A method for dividing the particulate hydrous gel by a quantitative feeder.

(a-6) A method for cutting a sheet-like gel obtained by belt polymerization.

Among them, it is preferable that at least the particulate water absorbent resin after drying is divided and in order for that, the polymerization gel or the particulate dried product is divided.

A preferable value of the dividing ratio of the particulate water absorbent resin and the polymerization gel to be divided in the mode is as described above.

Among them, the means (a-1) to (a-3) are preferably employed and the means (a-1) is more preferably employed in terms of the quantitative supplying property.

(b) Hopper

In terms of the surface-crosslinking property in the present invention, a hopper is preferable to be used before and after the surface-crosslinking. The hopper to be employed is more preferably a hopper with an inverse truncated pyramidal shape, an inverse circular truncated conical shape, a shape formed by adding a square pillar with the same shape as the maximum diameter part of an inverse truncated pyramid to the pyramid, a shape formed by adding a cylindrical column with the same shape as the maximum diameter part of an inverse circular truncated cone to the cone. The material thereof is not particularly limited; however, a hopper made of stainless steel is preferable to be employed and the surface roughness thereof is preferably within the above range. A preferable hopper and the shape thereof are exemplified in PCT/JP 2009/54903 and such a hopper is recommended.

(c) Transportation of Water Absorbent Resin Before and after Surface-Crosslinking Various kinds of methods may be employed as a method of transporting the water absorbent resin before and after surface-crosslinking, and preferably pneumatic transportation is employed. From a viewpoint that the excellent physical properties of the water absorbent resin particles and/or water absorbent resin powder can be maintained stably and the obstruction phenomenon can be suppressed, dried air is preferable to be employed as primary air and secondary air used based on the necessity (additional air for pneumatic transportation). The dew point of the air is generally −5° C. or lower, preferably −10° C. or lower, more preferably −12° C. or lower, and particularly preferably −15° C. or lower. The range of the dew point is −100° C. or higher, preferably −70° C. or higher, and it is sufficient about −50° C. in consideration of cost. Further, the temperature of the gas is 10 to 40° C. and more preferably about 15 to 35° C. The adjustment of the dew point of compressed air to be used at the time of pneumatic transportation to the above range can suppress a decrease in SFC, especially, at the time of wrapping the water absorbent resin as a product and thus, it is preferable.

Besides the use of the dried gas (air), heated gas (air) may be used. A heating method is not particularly limited and a gas (air) may be directly heated using a heat source or the transportation part or pipe may be heated to indirectly heat a gas (air) flowing therein. The temperature of the heated gas (air) is preferably 20° C. or higher and more preferably 30° C. or higher, and preferably lower than 70° C. and more preferably lower than 50° C.

A method of controlling the dew point, a gas, preferably air, may be dried properly. Specifically, examples thereof include a method using a membrane drier, a method using a cooling and adsorption type drier, a method using a diaphragm drier, or a method using these methods in combination. In the case where an adsorption type drier is used, it may be of thermal regeneration manner, a non-thermal regeneration manner, or a non-regeneration manner.

(6) Other Steps

Besides the above-mentioned steps, as required, a recycling step of the evaporated monomer, a granulating step, a fine powder removing step, a fine powder recycling step, etc. may be added. Further, in order to exhibit the effect of color stabilization over time, prevent gel deterioration, or the like, an additive described below may be used for the monomer or the polymer thereof.

[3] Polyacrylic Acid (Salt)-Type Water Absorbent Resin (1) Physical Properties of Polyacrylic Acid (Salt)-Type Water Absorbent Resin In the case the purpose is to use the polyacrylic acid (salt)-type water absorbent resin of the present invention for a sanitary material, particularly a paper diaper, it is preferable to control at least one of the following (a) to (e), further two or more including AAP, and still more three or more by the above-mentioned polymerization and surface-crosslinking. In the case the followings are not satisfied, the water absorbent resin sometimes fails to exhibit sufficient function in form of a high concentration diaper described below. The production method of the present invention is more effective for producing a water absorbent resin attaining the following physical properties and particularly for improving and stabilizing the physical properties (narrowing the standard deviation). That is, among the following physical properties of interest, the production method of the prevent invention is preferably applied to a method for producing a water absorbent resin having a water absorption against pressure (AAP) of 20 g/g or higher for an aqueous 0.9 mass % sodium chloride solution at a pressure of 4.8 kPa, a 0.69 mass % physiological saline flow conductivity (SFC) of 1 ($\times 10^{-7} \cdot cm^3 \cdot s \cdot g^{-1}$) or higher, and a water absorption under no pressure (CRC) of 20 g/g or higher, and more preferably applied to a production method within the following range to improve or stabilize the physical properties.

(a) Water Absorption Against Pressure (AAP)

In order to prevent leakage in a diaper, the water absorption against pressure (AAP) for an aqueous 0.9 mass % sodium chloride solution under a pressure of 1.9 kPa and that of 4.8 kPa is controlled to be preferably 20 g/g or higher, more preferably 22 g/g or higher, and still more preferably 24 g/g or higher as one example of means for accomplishing the surface-crosslinking and the cooling step carried out thereafter. The AAP is more preferable as it is higher; however, in terms of the balance between other physical properties and cost, the upper limit of the AAP is about 40 g/g at 1.9 kPa and about 30 g/g at 4.8 kPa. The AAP is shown as a value at 4.8 kPa unless otherwise specified.

(b) Liquid Permeability (SFC)

In some cases, in order to prevent a leakage from a diaper, the liquid permeability under pressure, which is a flow conductivity SFC (defined in U.S. Pat. No. 5,669,894) to a 0.69 mass % physiological saline flow conductivity (SFC) is controlled to be 1 ($\times 10^{-7} \cdot cm^3 \cdot s \cdot g^{-1}$) or higher, preferably 25 ($\times 10^{-7} \cdot cm^3 \cdot s \cdot g^{-1}$) or higher, more preferably 50 ($\times 10^{-7} \cdot cm^3 \cdot s \cdot g^{-1}$) or higher, still more preferably 70 ($\times 10^{-7} \cdot cm^3 \cdot s \cdot g^{-1}$) or higher, and particularly preferably 100 ($\times 10^{-7} \cdot cm^3 \cdot s \cdot g^{-1}$) or higher as one example of means for accomplishing the surface-crosslinking and the cooling step carried out thereafter.

In order to more effectively improve the liquid permeability, especially to improve SFC to 25 ($\times 10^{-7} \cdot cm^3 \cdot s \cdot g^{-1}$) or higher, the present invention is preferably applied for producing a water absorbent resin with high liquid permeability.

(c) Water Absorption Under No Pressure (CRC)

Water absorption under no pressure (CRC) is controlled to be preferably 10 (g/g) or higher, more preferably 20 (g/g) or higher, still more preferably 25 (g/g) or higher, and particularly preferably 30 (g/g) or higher. The CRC is more preferable as it is higher, and the upper limit is not particularly limited; however, in consideration of balance with other physical properties, it is preferably 50 (g/g) or lower, more preferably 45 (g/g) or lower, and still more preferably 40 (g/g) or lower.

(d) Amount of Water Soluble Components (Dissolve Amount)

The amount of water soluble components is preferably 0 to 35 mass %, more preferably 25 mass % or lower, still more preferably 15 mass % or lower, and still particularly preferably 10 mass % or lower.

(e) Residual Monomer

Using the above-mentioned polymerization as one example of achieving means, the amount of the residual monomer is adjusted to be generally 500 ppm by mass or lower, preferably 0 to 400 ppm by mass, more preferably 0 to 300 ppm by mass, and particularly preferably 0 to 200 ppm by mass.

(2) Other Additives

Further, in accordance with the purpose, 0 to 3 mass % and preferably 0 to 1 mass % of an oxidizing agent, an antioxidant, water, a polyvalent metal compound, a water-insoluble inorganic or organic powder such as silica and metal soap, etc. as well as a deodorant, an antibacterial agent, a polymer polyamine, pulp, and thermoplastic fibers, etc. may be added to the water absorbent resin.

(3) Purpose of Use

The purpose of use of the polyacrylic acid (salt)-type water absorbent resin of the present invention is not particularly limited; however, it is preferable to use the water absorbent resin for an absorbing article such as a paper diaper, a sanitary napkin, an incontinence pad, or the like. Particularly, the water absorbent resin exhibits excellent performance in case of being used in a high-consistency diaper (one diaper in which a large amount of the water absorbent resin is used) that conventionally has a problem of malodor and coloring derived from raw materials and particularly in the case of being used in a top layer part of an absorbent body of the absorbing article.

The content (core concentration) of the water absorbent resin in the absorbent body which may contain arbitrarily other absorbing materials (pulp fibers or the like) in the absorbing article is 30 to 100 mass %, preferably 40 to 100 mass %, more preferably 50 to 100 mass %, still more preferably 60 to 100 mass %, particularly preferably 70 to 100 mass %, and most preferably 75 to 95 mass % to exhibit the effect of the present invention. For example, in the case where the water absorbent resin of the present invention is used especially for an upper layer part of an absorbent body in the above concentration, the water absorbent resin is excellent in the dispersion property of an absorbed liquid such as urine or the like owing to the high liquid permeability (liquid permeability against pressure) and therefore, an absorbent product such as paper diaper can efficiently distribute a liquid and improve the amount absorbed by the whole of the absorbent product. Additionally, since the absorbent body keeps highly advanced white color, an absorbent product with sanitary impression can be provided.

EXAMPLES

Hereinafter, the effects of the present invention will be made apparent by way of examples; however, the present invention should not be construed in a limited way based on the description of the examples.

Production Example 1

Production of Water Absorbent Resin Particle (A)

A continuous production apparatus for a polyacrylic acid (salt)-type water absorbent resin was used which was obtained by connecting respective apparatuses for a polymerization step (static polymerization on a belt), a gel shredding step (pulverization step), a drying step, a crushing step, a classification step, and a transportation step between the respective steps and which could carry out the respective steps continuously. The production capacity of this continuous production apparatus was about 1500 kg per an hour. Water absorbent resin particles were continuously produced by using this continuous production apparatus.

First, an aqueous acrylic acid sodium salt solution partially neutralized at 75 mol % was prepared as an aqueous monomer solution (1). The aqueous monomer solution (1) contained 0.06 mol % of polyethylene glycol diacrylate (average n number=9) as an inner crosslinking agent relative to the total mole number. The concentration of the monomer (partially neutralized acrylic acid sodium salt) in the aqueous monomer solution (1) was 38 mass %. The obtained aqueous monomer solution (1) was continuously fed onto a belt by a constant rate pump. Nitrogen gas was continuously blown in the middle of the pipe used for the feeding and the oxygen concentration dissolved in the aqueous monomer solution (1) was adjusted to 0.5 mg/L or lower. In addition, the above-mentioned "average n number" means the average number of degree of methylene chain polymerization in the polyethylene glycol chain.

Next, sodium persulfate and L-ascorbic acid were continuously mixed by line mixing with the aqueous monomer solution (1). In this line mixing, the mixing ratio of the sodium persulfate was adjusted to 0.12 g per one mole of the monomer and the mixing ratio of the L-ascorbic acid was adjusted to 0.005 g per one mole of the monomer. The continuously mixed material obtained by line mixing was supplied in a thickness of about 30 mm to a flat plane steel belt having banks in both ends and subjected continuously to static aqueous solution polymerization for about 30 minutes to obtain a hydrous gel-like crosslinked polymer (1). The hydrous gel-like crosslinked polymer (1) was finely shredded into about 2 mm by a meat chopper with a hole diameter of 7 mm, spread on a movable porous plate of a continuous ventilating band drier in such a manner that the thickness thereof was adjusted to 50 mm, and dried at 185° C. for 30 minutes to obtain a dried polymer. The entire amount of the dried polymer was continuously supplied to a three-step roll mill, followed by crushing. Herein, the time taken from the outlet of the polymerization apparatus to the inlet of the drier was within 1 minute. The roll gaps of the three-step roll mill were 1.0 mm/0.55 mm/0.42 mm in this order from the upper side. After the crushing, the crushed polymer was classified by a sieving apparatus having metal sieving nets with 850 μm meshes and 150 μm meshes to obtain water absorbent resin particles (A) containing about 98 mass % of particles having a particle diameter of 150 to 850 μm. The CRC of the water absorbent resin particles (A) was 35 g/g and the bulk specific gravity thereof was 0.6 g/cm$^3$.

Example 1

A water absorbent resin powder (1) was produced by using a continuous production apparatus involving a surface treatment step (wetting and mixing step, heating step, and cooling step), a particle regulation step, and a transportation step connecting the respective steps, successively from the continuous production apparatus used in Production Example 1. That is, the classification step of Production Example 1 and the surface treatment step were connected by the transportation step.

The water absorbent resin particles (A) were pneumatically transported by pneumatic transportation (temperature 35° C. and dew point −15° C.) from the classifying apparatus to a high speed continuous mixing apparatus (Turbulizer; 1000 rpm; e.g., FIG. 3) continuously supplied at 1.5 t/hr and at the same time a surface treatment agent solution (1) was mixed by spraying (wetting and mixing step). The temperature of the inner wall of the mixing apparatus was controlled to be 70° C.; the temperature of the gas current in the device was controlled to be 65° C.; the pressure reduction degree was controlled to be 0.3 kPa; and the stirring shaft was heated to 150° C. (+80° C. from the inner wall temperature of 70° C.). The surface treatment agent solution (1) was a mixed solution containing 1,4-butanediol, propylene glycol, and pure water. The surface treatment agent solution (1) was mixed with the water absorbent resin particles (A) at a ratio of 0.3 parts by mass of 1,4-butanediol, 0.5 parts by mass of propylene glycol, and 2.7 parts by mass of pure water relative to 100 parts by mass of the water absorbent resin particles (A) to give a mixture (1), a wet powder. The temperature of the mixture (1) is at 70° C.

The obtained mixture (1) was then surface-treated by a transverse type continuous stirring apparatus (1) having a downward inclined angle of 1°, an aspect ratio of 2.2, a paddle rotation speed of 13 rpm, two rotary shafts, and stirring disks having scraping blades, and a surface roughness (Rz) of the inner surface of 500 nm (heat treatment step). At that time, the inside of the apparatus (1) was suctioned by a suctioning gas discharge apparatus having a bag filter, and the inside pressure of the apparatus was reduced to 1 kPa. A rotary valve (periodically shielding apparatus) was installed in the inlet (connecting part with the mixing apparatus) and outlet (connecting part with the cooling apparatus) of the apparatus (1). According to a previous test, the position of a discharge bank which gave an average retention time of about 45 minutes and an average filling ratio of 75% was measured, and the discharge bank was set at the position as measured. A heating source used for the surface treatment was pressurized steam at 2.5 MPa, and the temperature of the mixture (1) in the apparatus was measured by a thermometer installed near the discharge part of the transverse type continuous stirring apparatus (1), and the steam flow rate was controlled to carry out the heating in such a manner that the temperature was adjusted to 198° C. The total surface area of the stirring disks and the stirring shafts was 24.4 m$^2$ and the mass surface area ratio calculated from the total surface area (heat transfer surface area) and the treatment amount was 61.5 kg/m$^2$/hr. The stirring power at the time of the surface treatment was 27.8 kW, the stirring power in idling was 13.5 kW, the average retention time was 45 minutes, and the stirring power index was 9.5 W·hr/kg. The rotary valve used had 300 angles (mm) and a capacity of 3 t/hr.

Using a similar (slightly compact) transverse type continuous stirring device, it was then cooled forcibly to 60° C. (cooling step). The stirring power index was 8.5 W·hr/kg.

The water absorbent resin discharged was classified by a sieving apparatus to separate the substance under 850 μm, and the substance on 850 μm (substance not passed through 850 μm) was again crushed and mixed with the substance under 850 μm to give a water absorbent resin powder (1), as a particle size-regulated product which was the total amount of the substance under 850 μm.

The obtained water absorbent resin powder (1) had a CRC of 30.2 (g/g), an SFC of 29.9 ($\times 10^{-7}$·cm$^3$·s·g$^{-1}$), an AAP of 25.1 (g/g). The standard deviation of each physical property value was CRC: 0.18, SFC: 0.45, and AAP: 0.21. Additionally, these physical property values were average values of the measurement carried out by sampling (5 points) every 2 hours until 10 hours were passed from the starting of the operation. Physical property values are measured in the following examples and comparative examples as same manner as conducted in this example. The results are shown in Table 1.

Example 2

Operations were carried out in the same manner as in Example 1 to obtain a water absorbent resin powder (2), except that the surface-crosslinking step was carried out in 2 lines in parallel (that is, two of the mixing apparatuses, the heating apparatuses, and the cooling apparatuses are arranged in parallel) against 1 line of the polymerization step. The obtained water absorbent resin powder (2) had a CRC of 30.3 (g/g), SFC of 29.7 ($\times 10^{-7} \cdot cm^3 \cdot s \cdot g^{-1}$) and AAP of 25.2 (g/g). The standard deviation of each physical property value was CRC: 0.15, SFC: 0.40, and AAP: 0.15. The results are shown in Table 1.

Comparative Example 1

The same operation was carried out as in Example 1 to obtain a water absorbent resin powder (3), except that the temperature in the inside of the high speed continuous stirring device was controlled to be 38° C. and the stirring shaft was not heated in Example 1.

The obtained water absorbent resin powder (3) had a CRC of 30.4 (g/g), SFC of 28.1 ($\times 10^{-7} \cdot cm^3 \cdot s \cdot g^{-1}$) and AAP of 24.4 (g/g). The standard deviation of each physical property value was CRC: 0.44, SFC: 1.46, and AAP: 0.29. The results are shown in Table 1.

C. was used. The SFC after the pneumatic transportation was 28.3 and the SFC decrease ratio was 4.7%.

Example 5

In Example 1, the high speed continuous mixing apparatus (Turbulizer; 1000 rpm) was changed to a hoe type blender (Lodige mixer (e.g., FIG. 1); 400 rpm; surface roughness (Rz) of inner face was 400 nm); and also the surface treatment agent solution (1) in Example 1 was changed to a surface treatment solution (2) containing 0.3 parts by mass of 1,4-butanediol, 0.6 parts by mass of propylene glycol, and 3.5 parts by mass of pure water (the amount to 100 parts by mass of the water absorbent resin particles (A)). Herein, the temperature of the inner wall of the mixing apparatus was controlled to be 90° C.; the temperature of the gas current in the device was controlled to be 65° C.; the pressure reduction degree was controlled to be 0.3 kPa; and the stirring shaft was heated to 150° C. (+80° C. from the inner wall temperature of 70° C.). The temperature of the obtained mixture (2) was increased more than that before mixing by 1° C. A water absorbent resin powder (4), as a particle size-adjusted product which was the total amount of the substance under 850 μm, was obtained by carrying out the heating treatment step, the cooling step, and the granulation step (classification step) as in Example 1.

The water absorbent resin (4) had CRC=30.1 (g/g), SFC=33.0 ($\times 10^{-7} \cdot cm^3 \cdot s \cdot g^{-1}$), and AAP=25.3 (g/g), and the standard deviation was 0.19 for CRC, 0.47 for SFC, and 0.22 for AAP, respectively.

TABLE 1

|  |  | Example 1 | Example 2 | Comparative Example 1 | Example 5 |
|---|---|---|---|---|---|
| mixing apparatus type |  | High speed continuous blender | High speed continuous blender | High speed continuous blender | Hoe type blender |
| shaft temperature | [° C.] | 150 | 150 | without heating | 90 |
| temperature in the inside of the device | [° C.] | 65 | 65 | 38 | 65 |
| water absorbent resin powder physical properties |  | (1) | (2) | (3) | (4) |
| CRC | [g/g] | 30.2 | 30.3 | 30.4 | 30.1 |
| SFC | [$\times 10^{-7} \cdot cm^3 \cdot s \cdot g^{-1}$] | 29.9 | 29.7 | 28.1 | 33.0 |
| AAP | [g/g] | 25.1 | 25.2 | 24.4 | 25.3 |
| standard deviation |  |  |  |  |  |
| CRC |  | 0.18 | 0.15 | 0.44 | 0.19 |
| SFC |  | 0.45 | 0.40 | 1.46 | 0.47 |
| AAP |  | 0.21 | 0.15 | 0.29 | 0.22 |

Example 3

The water absorbent resin powder (2) obtained in Example 2 was pneumatically transported by allowing compressed air (dew point −15° C. and temperature 35° C.) to flow in a pipe with a surface roughness (Rz) of 200 nm in the inner surface and wrapped. The SFC after the pneumatic transportation was 29.2 ($\times 10^{-7} \cdot cm^3 \cdot s \cdot g^{-1}$) and the SFC decrease ratio was 1.7%.

Example 4

The same pneumatic transportation as in Example 3 was carried out, except that compressed air with a dew point of 20°

Comparative Example 2

In Example 5, in the case where the heating of the stirring shaft was not carried out, the water absorbent resin was stuck to the shaft and hoe blades and the operation time was prolonged and the physical properties were deteriorated (AAP was decreased by 0.1 to 1.0 points and SFC was decreased by a few points). Further, in the case of continuous operation for 12 hours, due to an over load caused by the adhesion of the water absorbent resin, the mixing apparatus was stopped. It was understood that a significant effect was exerted by heating the shaft in a hoe type blender.

Comparative Example 3

In Example 5, in the case where the stirring shaft was coated with Teflon (polytetrafluoroethylene) in place of heating of the stirring shaft, the water absorbent resin was gradually stuck to the shaft and hoe blades due to peeling of the Teflon and the physical properties were gradually deteriorated for every several months in Comparative Example 3 (AAP was decreased by 0.1 to 1.0 points and SFC was decreased by a few points), whereas the physical properties were stable in Example 5 and therefore, it was needed to stop the continuous operation and carry out coating again with a Teflon resin.

(Conclusion)

Table 1 shows physical property deflection (standard deviation) in continuous 10 hour operation and physical properties (average value). Table 1 shows the results (average value and standard deviation) of analysis of the products for every 2 hours.

As shown in Table 1, it was found that the physical properties of the water absorbent resin were improved and stabilized (decrease of standard deviation) by heating the stirring shaft of a continuous mixing apparatus for the surface-crosslinking agent in the wetting and mixing step and controlling the device inner temperature to be 40° C. or higher.

It was also understood from the results of Example 3 and Example 4 that pneumatic transportation using compressed air with a specified dew point was preferable.

(Comparison with Conventional Techniques)

The physical properties of a water absorbent resin were improved and stabilized (decrease of standard deviation) by heating the stirring shaft or controlling the temperature of gas current in this application, as compared with those in the above-mentioned Patent Documents 1 to 41, conventional surface treatment techniques. For improvements in the device, for example, techniques of using specified mixing apparatuses for surface-crosslinking agents (Patent Documents 26 to 29) are known and also known are techniques of heating devices (Patent Documents 30 and 31), for example, U.S. Pat. No. 6,576,713 discloses a technique of using a stirring mixing apparatus in which the inner wall temperature of the mixing apparatus is controlled to be 40° C. or higher in claim 16; however, such improvements in the device are made without paying attention to the heating of the shaft and blades and to the temperature or pressure of the inner gas current and thus do not imply the present application and correspond to Comparative Examples in the present invention.

INDUSTRIAL APPLICABILITY

A water absorbent resin with high physical properties, particularly, high liquid permeability is provided by continuous production in a huge scale (e.g., 1 t/hr or more).

EXPLANATION OF REFERENCE NUMERALS

10: Operation device
20: Transverse type drum
30: Raw material supply port
40: Nozzle for supplying water-based solution
50: Discharge port
60: Inner wall
63: Bank
70: Stirring shaft
73: Hoe type stirring blade

The invention claimed is:

1. A method for producing a polyacrylic acid (salt)-type water absorbent resin comprising steps of:
    preparing an aqueous monomer solution of an acrylic acid (salt),
    continuously polymerizing the aqueous monomer solution into a hydrous gel-like crosslinked polymer,
    finely shredding the hydrous gel-like crosslinked polymer during or after polymerization,
    drying the obtained particulate hydrous gel-like crosslinked polymer to obtain a dried water absorbent resin powder,
    adding a surface-crosslinking agent to the dried water absorbent resin powder with a continuous mixing apparatus, wherein the pressure inside of the continuous mixing apparatus is a reduced pressure greater than 0 kPa and is 10 kPa or lower than atmospheric pressure, and
    carrying out reaction of the mixture, wherein
    a stifling shaft of the continuous mixing apparatus for the surface-crosslinking agent is heated in the step of mixing the surface-crosslinking agent.

2. A method for producing a polyacrylic acid (salt)-type water absorbent resin comprising steps of:
    preparing an aqueous monomer solution of an acrylic acid (salt),
    continuously polymerizing the aqueous monomer solution into a hydrous gel-like crosslinked polymer,
    finely shredding the hydrous gel-like crosslinked polymer during or after polymerization,
    drying the obtained particulate hydrous gel-like crosslinked polymer to obtain a dried water absorbent resin powder,
    adding a surface-crosslinking agent to the dried water absorbent resin powder with a continuous mixing apparatus, and
    carrying out reaction of the mixture, wherein
    the continuous mixing apparatus for the surface-crosslinking agent is operated at below ambient pressure and at a gas current of at least 40° C. to adjust the outlet gas temperature of the gas current in the mixing apparatus during mixing the surface-crosslinking agent, wherein the pressure inside of the continuous mixing apparatus is a reduced pressure greater than 0 kPa and is 10 kPa or lower than atmospheric pressure.

3. The production method according to claim 1 or 2, wherein the stirring shaft of the continuous mixing apparatus for the surface-crosslinking agent is so heated as to be at a higher temperature than the inner wall temperature of the continuous mixing apparatus.

4. The production method according to claim 1 or 2, wherein the pressure of the inside of the continuous mixing apparatus for surface-crosslinking agent is reduced.

5. The production method according to claim 1 or 2, wherein 50 to 100% in the inner surface area of the continuous mixing apparatus is of a metal.

6. The production method according to claim 1 or 2, wherein the inner face of the inside of the continuous mixing apparatus for the surface-crosslinking agent is of a stainless steel with a surface roughness (Rz) of 800 nm or lower.

7. The production method according to claim 1 or 2, wherein the reaction step for the mixture is carried out at 150° C. to 250° C.

8. The production method according to claim 1 or 2, wherein the water absorbent resin powder is pneumatically transported by using compressed air with a dew point of −5° C. to −100° C.

9. The production method according to claim 1 or 2, wherein the mixing apparatus is a hoe type blender.

10. The production method according to claim 1 or 2, wherein the temperature of the mixture is 50 to 95° C. until the mixture flows to the reaction step after the surface-crosslinking agent is mixed.

11. The production method according to claim 1 or 2, wherein the reaction step of the mixture has two or more lines in the polymerization step.

12. The production method according to claim 1 or 2, wherein the average residence time of the water absorbent resin in the continuous mixing apparatus is within 1 minute.

13. The production method according to claim 1 or 2, wherein the temperature of the mixture is increased by 0.5° C. or more by continuously mixing the crosslinking agent to the dried water absorbent resin powder.

14. The production method according to claim 1 or 2, wherein the water absorbent resin has 20 g/g or higher of water absorption against pressure (AAP) for an aqueous 0.9 wt. % sodium chloride solution at a pressure of 4.8 kPa, 1 ($\times 10^{-7} \cdot cm^3 \cdot s \cdot g^{-1}$) or higher of saline flow conductivity of 0.69 wt. % physiological saline solution (SFC), and 20 g/g or higher of water absorption under no pressure (CRC).

* * * * *